(12) United States Patent
Baron et al.

(10) Patent No.: US 7,732,157 B1
(45) Date of Patent: Jun. 8, 2010

(54) SOLUBLE EPIDERMAL GROWTH FACTOR RECEPTOR-LIKE PROTEINS AND THEIR USES IN CANCER DETECTION METHODS

(75) Inventors: Andre T. Baron, Rochester, MN (US); Nita J. Maihle, Rochester, MN (US)

(73) Assignee: Tumor Biology Investment Group, Rochester, MN (US)

( * ) Notice: Subject to any disclaimer, the term of this patent is extended or adjusted under 35 U.S.C. 154(b) by 0 days.

(21) Appl. No.: 09/676,380

(22) Filed: Sep. 29, 2000

Related U.S. Application Data

(60) Provisional application No. 60/157,144, filed on Sep. 30, 1999.

(51) Int. Cl.
*G01N 33/50* (2006.01)
*G01N 33/53* (2006.01)
*G01N 33/574* (2006.01)

(52) U.S. Cl. .................... 435/7.92; 435/7.94
(58) Field of Classification Search .............. 435/7.1, 435/7.23; 429/9.1; 530/350, 388.1
See application file for complete search history.

(56) References Cited

FOREIGN PATENT DOCUMENTS

WO      WO 94/11734     *   5/1994

OTHER PUBLICATIONS

Graus-Porta et al., EMBO J., 1997, vol. 16, pp. 1647-1655.*
Olayioye et al., J. Biol. Chem., 1999, vol. 274, pp. 17209-17218.*
Sobol et al. J Natl Cancer Inst. 1987; 79: 403-405.*
Ulbright TM. Mod Pathol. 2005;18 Suppl 2: S61-79.*
Meienhofer, "Hormonal Proteins and Peptides," ed. "Peptide Synthesis: A Review of the Solid Phase Method," 1973, vol. 2, Li (ed.), Academic Press, pp. 45-267.

* cited by examiner

*Primary Examiner*—Bridget E Bunner
*Assistant Examiner*—Christina Borgeest
(74) *Attorney, Agent, or Firm*—Cohen & Grigsby, P.C.

(57) ABSTRACT

The present invention relates to the discovery of soluble isoforms of an Epidermal Growth Factor Receptor, or sErbB 1/HER1 variants, the provision of the sequences of nucleic acids encoding these isoforms, purified recombinant proteins, novel antibodies specific for these isoforms, and the use of immunoassay and gene expression assay techniques to measure the concentration of these gene products in a patient biological sample. The present invention also provides methods for determining the presence of an ovarian carcinoma in the patient by assaying the concentration of soluble EGFR/ErbB1 variants in a biological sample from a patient.

Figure 1:
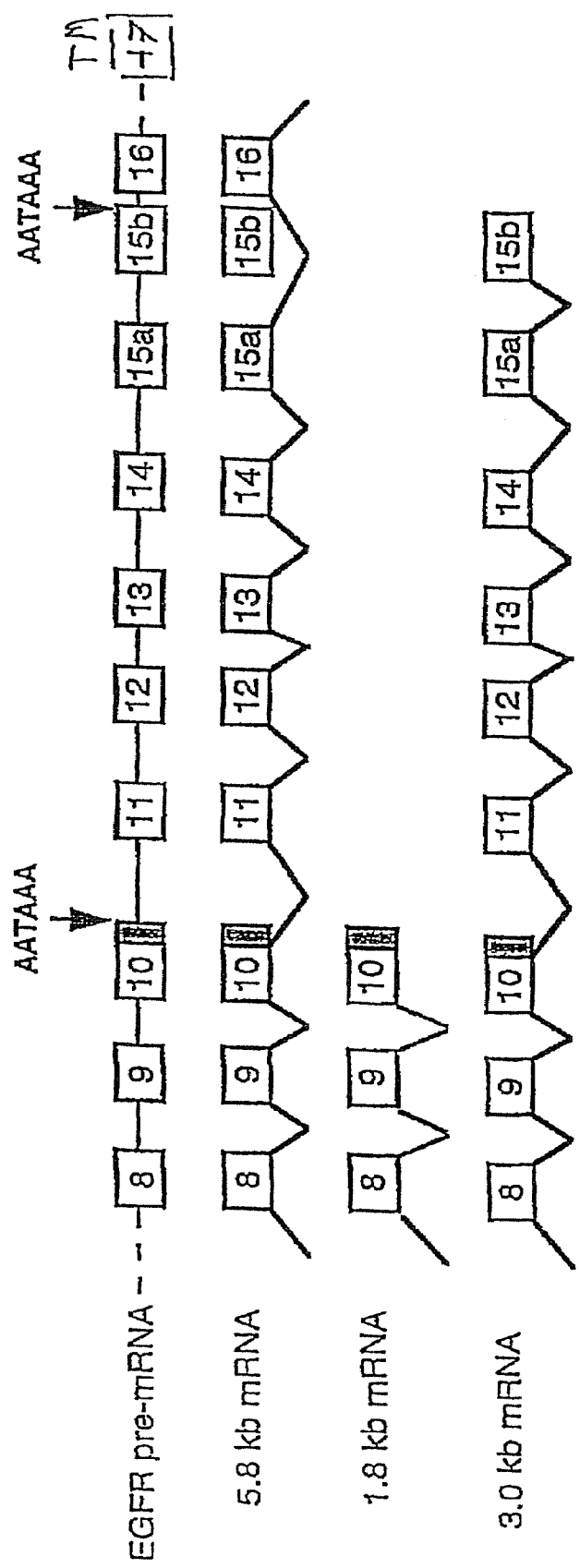

15 Claims, 16 Drawing Sheets p60 ErbB1-S

- encoded by 1.8 kb transcript
- mature product = 60 kDa
- Contains 381 amino acids
  – unique a.a: Leu and Ser
- Calculated mw = 45 kDa:
  – minus signal peptide = 42 kDa p110 ErbB1-S

- encoded by 3.0 kb transcript
- mature product = 110 kDa
- Contains 681 amino acids
  – 78 unique a.a
- Calculated mw = 77 kDa
  – minus signal peptide = 75 kDa

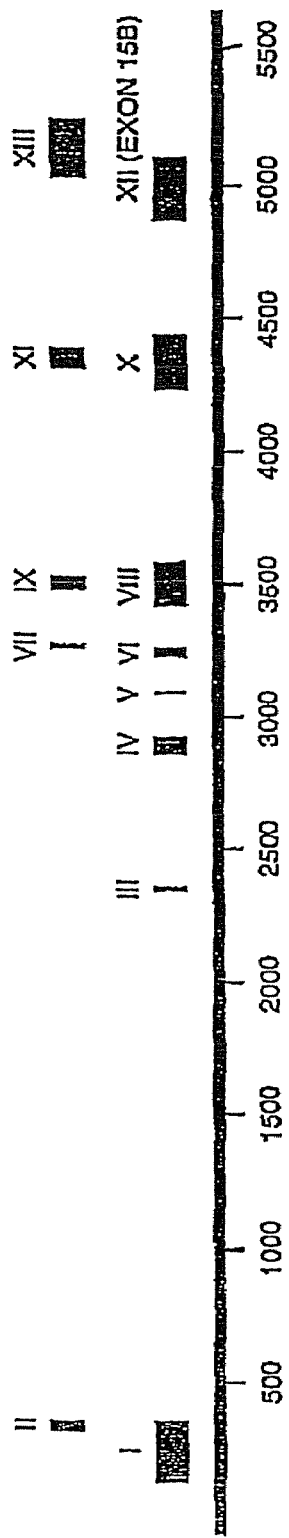
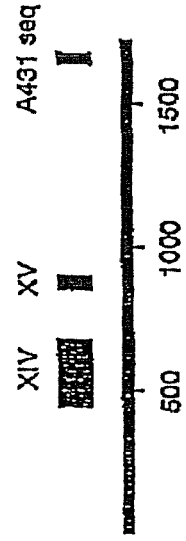
FIGURE 3

| Seq ID | Alternative exons (coding sequence only) | IVS # | Amino Acids | Translated Peptides |
|---|---|---|---|---|
| Exon 15 | cag GGACCAGAGACAACTGTATCCAGTGTGCCCACTACATTGACGGGCCCCACTG CGTCAAGACCTGCCCGGCAGGAGTCATGGGAGAAACAACACCCTGGTCTGAAG TACGCAGAGCGCCGGCCATGTGTGCCACTGTGCCATCCAAACTGCACCTACGG SEQ ID NO: 38 | NA | 53 | GPDNCIQCAHVIDGPHCVKTCP AGVMGENNTLVWKYADAGHVCH LCHPNCTYG SEQ ID NO: 21 |
| I | cag CCAATGCCAGTAGCAACTTGCTTGTGAGCAGGCCTCAGTGCAGTGGGAATG ACTCTGCCATGCACCGTGCCCCGGCCTGTGTTGTGCAATGCTGCACAT CACAACAGGAGGTAGGGGAGCAAAAGACACAGTGCCTGGCAGTGCCACAGT CTCCAGGGCTTATGCTTTCTCTCAAGATTTCTAAGGTTAACATGGGATTAG CTGTTTGCAATGA SEQ ID NO: 39 | 139-364 | 74 | HASSNLLVSRPQCSGNDSAMHR VPGRACVVQCCTSQQEGRGTHE HRSWQLPQSPGAFAPLSRFLRL TWGLAVLQ* SEQ ID NO: 22 |
| II | cag ATTTCTAAGGTTAACATGGGATTAGCTGTTTGCAATGA SEQ ID NO: 40 | 325-364 | 12 | PLRLTWGLAVLQ* SEQ ID NO: 23 |
| III | tag GAAAACAATCATATAA SEQ ID NO: 41 | 2342-2357 | 4 | KTII* SEQ ID NO: 24 |
| IV | cag ATGTTGCATCAGTATCTCTGCATCAATATCTCTATATACAGTATCTCTGTGT CAGTGAGCATATGTTGCTGGGCTAG SEQ ID NO: 42 | 2857-2932 | 24 | CASVSLHQYLYISISVSVSICC WA* SEQ ID NO: 25 |
| V | cag GTCCTAA | 3086-3092 | 1 | G* |
| VI | tag TATGTGTGATTACATTCCTGATTCTGAGCCTTTTAG SEQ ID NO: 43 | 3229-3265 | 11 | MCDYIPDSEPF* SEQ ID NO: 26 |
| VII | tag ATAG | 3266-3269 | 0 | * |
| VIII | gag TATTTATGAGGTGCACAACATTCCTGAATACATATTCTCTCTCATTCTC AGATGGATGTATTGCCTTCTCCATTTCTATTGTTAAAGTAACACTTACAGGGG TTTCTTAACAACTTGTGAACAGAGCATCAGAGCCCAGACTACAGCATAAGCA GCTGCTGA SEQ ID NO: 44 | 3422-3587 | 54 | IYDVHNIPEYIVSLISQMGCIA FSISIVKETLTGVSLTTCEQQH QSPDYSISSC* SEQ ID NO: 27 |
| IX | cag ATGGATGTAATTGCCTTCTCCATTTCTATTGTTAAAGAAACACTTACAGG GGTTTCTTTAA SEQ ID NO: 45 | 3474-3534 | 19 | WDVIPSFLLLKKHLQGFL* SEQ ID NO: 28 |
| X | cag AGTTCCGAGGGCTCATCAGGCTGTCAGCAGGAGGAGCCCCTCGCCTTCTGACG CTCTCACATCCTTCTCTGCCAGCCCGTGCTGCCACTGCCTGTCCAGCTT CTCTTCAAGGGTCAACTGTCTACCTTCCCAAAAGCATTTCAGAGCCTGCATAA SEQ ID NO: 46 | 4233-4437 | 67 | VTEGLISVSRSPSPSDALTSTS PAAPSCHCPCPASLQGSTGLPF PTSLQLIVSNPYGCPKAPSEP A* SEQ ID NO: 29 |
| XI | cag CCCCGTCTCCTGCCACTGTCCTGTCCAGCTTCTCTTCAAGGGTCAACTGGT CTACCTTCCCTACAAGTCTGTCACAGCTTCTGTTAG SEQ ID NO: 47 | 4307-4394 | 28 | PVLPLSLSSFSSRVNWSTFPYK SVTASC* SEQ ID NO: 30 |
| XII (Exon 15B) | cag GCCAGGAAATGAGAGTCTCAAAGCCAATGTTATTCTGCCTTTTAAACTAT CATCCTGTAATCAAAGTAAATGAATGGCAGCAGTGCCCACAGACCCTCAGGTT CTGCTCAGGAGTCAATGCATGCTTAGGATGGATCCGCCTTCTTGCCGTCAGATTTC AGCTGGTTGGGGTGGATGCAGGCCACCTTCAATGCCTGGCCTTCTCTGCATCTGTGA TCATCACGGCCCCTCCTGCCACTGA SEQ ID NO: 48 | 4870-5107 | 78 | PGNESLKAMLFCLFKLSSCNQS NDGSVBHOSGSPAAQESCLGWI PSLLPSEFQLGWGGCSHLHAWP SASVITASSCH* SEQ ID NO: 31 |
| XIII | cag AGTTTCAGCTGGGTTGGGGTGGAATGCAGCCACCTCCATGCCTGGCCTTCT GCACTCTGATCATCACGGCCCCTCCTCCTGCCACTCAGCCTCATGCCTTCACGTG TCTGTTCCCCCGCTTTCCTTTCCTTCCTCACCCCGCAGGTTC CCAAGAGTATCCTACCCATTTCTTTCCTTCCTCCCTTTGCAGTGCCTCTCA CCCCAACTAGCTAA SEQ ID NO: 49 | 5022-5250 | 75 | VSAGLGWMQPPFCLAFCICDHH GLLFPLSLMPGRVCSTRFSFLP PLHVGRQVPKSILPISFLPLPL PVPLTPFSS* SEQ ID NO: 32 |
| Exon 16 | cag ATGCACTGGGCCAGTGTCTTGAAGGCTGTGCCAACGAATGG SEQ ID NO: 50 | NA | 13 | CTGPGLEGCPTNG SEQ ID NO: 33 |

FIGURE 4A

| | | | |
|---|---|---|---|
| XIV | cag ACACACTGCCCAGCAAGGCAAAAGGGCTTCTTCAACATCAGCTCTGGC CAGTTTGCCAGAGCAAAGCCCTGAGAAAACAGGTTGAAAAGTCTTATTCAAA CTCACCAGGAAAAGAGTGGTGTTACTCTCGATGGCGTCTAGCCAGAATCATGGA ATTATACACCGAGCACCTGTTTGCCATTTTGGATGTTTCCAAACATGAACCAAA CTTCCAGGCCCCTCTGCCATCTCTGGTAA SEQ ID NO: 51 | 444-684 | 79 | HTAQQRQKGFLQHQLMFVCQSK ALAKARLKSLIQTHQERVVLLS MASSQESWNYTPSTCLPFWMFP NMNQTSRPLCHLW* SEQ ID NO: 34 |
| XV | cag TGAGCTGCTAGGACACCCAGCAGAACTTCCCACTCCACACTGCAATCTC AGGGATCTTAG SEQ ID NO: 52 | 849-909 | 19 | ELLGHPAELPHSTLQSQGS* SEQ ID NO: 35 |
| A431 aag | tag AAGCTACATAGTGTCTCACTTTCCAAGATCATTCTACAAGATGTCAGTGC ACTGA SEQ ID NO: 53 | 1633-1687 | 17 | SYIVSHFPRSFYKMSVH* SEQ ID NO: 36 |
| Exon 17 | cag GCCTAAGATCCCGTCCATCGCCACTGGCACTCGCCATCTGGGATGGTGGGGCCCTCCTCTTGC TGCTGGTGGTGGCCCTGGGGAATGCGGCCTCTTCATGCGAAGGCGGCCACATCGTTC GGAAGCGCACGCTGCGCCGCTGCGGGAGGCGTGCTGCCAGGAGGAGGGAG SEQ ID NO: 54 | NA | 47 | PKIPSIATGMVGNLLLLVVAL GIGLFMRRHIVRKRTLRRLLQ ERE SEQ ID NO: 37 |

FIGURE 4B

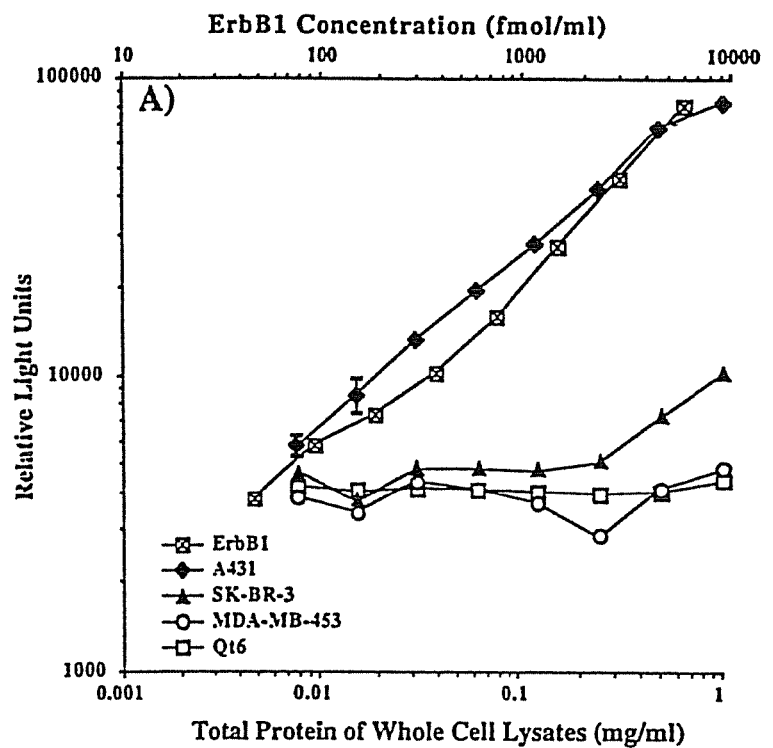
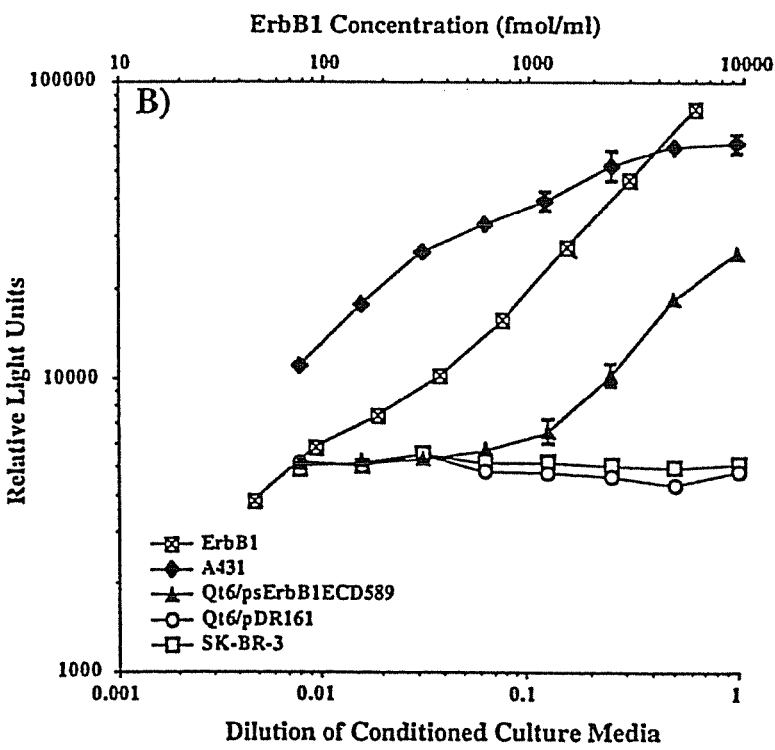
FIGURE 7

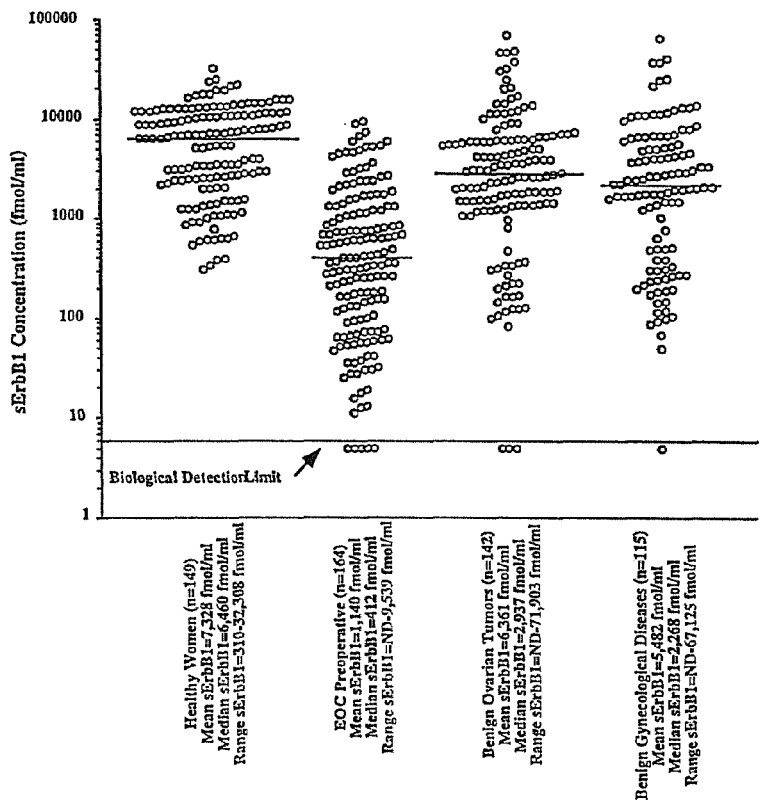

Serum sErbB1 levels in healthy women, patients with EOC, benign ovarian tumors, and other benign gynecological diseases as measured by ALISA and compared. Serum samples with sErbB1 levels below the inter-assay biological detection limit (horizontal line with arrow) of 5.89 fmol/ml were arbitrarily assigned values of 5.0 fmol/ml for graphing purposes. Each data point represents the median of the mean sErbB1 concentration for one serum sample tested in duplicate from a minimum of three separate assays. The median sErbB1 concentration for each group of patients is indicated by the horizontal line.

FIGURE 12

SOLUBLE EPIDERMAL GROWTH FACTOR RECEPTOR-LIKE PROTEINS AND THEIR USES IN CANCER DETECTION METHODS

This application claims priority from U.S. Application No. 60/157,144, filed Sep. 30, 1999, entitled "SOLUBLE EPIDERMAL GROWTH FACTOR RECEPTOR-LIKE PROTEINS AND THEIR USES".

The disclosed invention was made with the support of grants from the National Institutes of Health: K07 CA 76170 "Soluble ErbB1 Molecules as Tumor Biomarkers"; R03CA82091 "Serologic sErbB1 in Healthy Women"; R21CA82520 "Circulating sErbB1 Levels as Diagnostic Tumor Biomarkers"; R01CA57534 "Truncated c-erbB Receptors in Women with Ovarian Cancer"; and U01 CA85133 "Early Detection Research Network: National Ovarian Cancer Early Detection Program". The U.S. Government has certain rights in the invention.

FIELD OF THE INVENTION

The present invention relates to the discovery of soluble isoforms of an Epidermal Growth Factor Receptor ("sEGFR"), or sErbB1/sHER1 variants, the nucleic acid sequences encoding these isoforms, purified recombinant proteins, novel antibodies specific for these isoforms, and the use of immunoassay and other assay techniques to measure the concentration of these isoform[s] gene products in a patient biological sample. The present invention also provides diagnostic methods for assessing the risk of ovarian cancer or for determining the presence of an ovarian carcinoma in the patient by assaying the concentration of soluble EGFR/ErbB1 variants in a biological sample from a patient.

BACKGROUND OF THE INVENTION

The epidermal growth factor receptor (EGFR) is a transmembrane glycoprotein encoded by the EGFR/ERBB1/HER1 proto-oncogene. Sequence analysis demonstrated that the human EGFR is the cellular homolog of the v-erbB oncogene from the avian erythroblastosis retrovirus (Downward et al., Nature, 307, 521 (1984); Ullrich et al., Nature, 309, 418 (1984)). In recent years, a series of c-erbB related cell surface receptor tyrosine kinases has been identified. The four members of the ErbB proto-oncogene family are: ErbB1/EGFR/HER1, ErbB2/Neu/HER2 (Coussens et al., Science, 230, 1132 (1988)); ErbB3/HER3 (Kraus et al., Proc. Nat'l. Acad. Sci. USA, 86, 9193 (1989)); Plowman, et al., Proc. Nat'l. Acad. Sci. USA 87, 4905 (1990)); and ErbB4/HER4 (Plowman et al., Proc. Nat'l. Acad. Sci. USA, 90, 1746 (1993)). The Epidermal Growth Factor Receptor (EGFR/ErbB1/HER1) includes three functional domains: an extracellular ligand binding domain, a transmembrane domain, and a cytoplasmic tyrosine kinase domain. The extracellular domain can be further divided into four subdomains (I-IV), including two cysteine-rich regions (II and IV) and two flanking regions (I and III) (Lax et al., Cell Regul. 2,337 (1991)). Subdomains I and III are involved in ligand binding. Ligand binding to the receptor represents the first event in a complex cascade culminating in DNA synthesis and cell division as well as other events. The full-length 170 kD human EGFR is encoded by two alternatively spliced transcripts of 5.8 and 10.5 kb (Ullrich et al., supra). In addition, alternatively spliced mRNA's from the EGFR/ErbB1/HER1 gene also encode soluble forms of this receptor. An 80 kD EGFR isoform present in human placenta extracts may be encoded by an alternatively spliced 1.8 kb RNA transcript (Ilekis et al., Mol. Reprod. Devel., 41, 149 (1995)). Furthermore, soluble EGF receptors arise from aberrant transcription products in carcinoma-derived cell lines, as exemplified by the epidermoid carcinoma line, A431 (Ullrich et al., supra). In this cell line, the EGFR gene is amplified and rearranged, and a 2.8 kb transcript arises from a translocation between the 5'-region of the EGFR gene and an unidentified region of genomic DNA (Ullrich et al., supra; Merlino et al., Mol. Cell. Biol., 5, 1722 (1985); Hunts et al., Cell Mol. Genet., 11, 477 (1988)). Alternatively spliced EGFR/ErbB1RNA transcripts of approximately 1.8-2.8 kb that encode alternate receptor isoforms containing only the extracellular ligand binding domain are also found in normal human, chicken, rat and mouse tissues (Maihle et al. Proc. Nat'l Acad. Sci. USA, 88, 1825 (1991); Petch et al., Mol. Cell. Biol., 10, 2973 (1990); Flickinger et al., Mol. Cell. Biol., 12, 883 (1991); Das et al., Endocrinology 134, 971 (1994); Rho et al., Mol. Carcinogenesis. 11, 19 (1994); Reiter and Maihle, Nucl. Acids Res., 24, 4050 (1996); Tong et al., Endocrinology 137, 1492 (1996)).

Soluble isoforms of ErbB (sErbB) receptors are being investigated in connection with several cancers (McKenzie, Biochim. Biophys. Acta, 1072, 193 (1991); Brandt-Rauf, Mutat. Res., 333, 203 (1995)). Immunoassay studies show that sErbB2 proteins are elevated in serum samples of patients with breast and ovarian cancer (Mori et al., Jpn. J. Cancer. Res., 81, 489 (1990); Meden et al., Anticancer Res., 17, 757 (1997)). Recent studies suggest that low pretreatment serum sErbB2 levels are positive predictors of responsiveness to hormonal therapy for patients with metastatic breast cancer (Hayes et al., Breast Cancer Treat., 14, 135, (1993); Leitzel et al., J. Clin. Oncol., 13, 1129 (1995); Yamauchi et al., J. Clin. Oncol., 15, 2518 (1997)). Meden et al. (supra) have reported a positive association between elevated serum p105 sErbB2 levels and shorter survival for patients with stage I through IV epithelial ovarian cancer (EOC). In addition, U.S. Pat. No. 5,674,753, issued Oct. 7, 1997, described the use of antibodies against the external EGF binding domain of EGF receptors to diagnose neoplastic diseases correlated with an increase in the level of an EGF receptor in a patient's blood.

Immunoassay studies show that the extracellular domain of ErbB1 is detectable and increased in the serum of patients with asbestosis-induced lung cancer (Partanen et al., J. Occup. Med., 36, 1324 (1994); Partanen et al., Int. J. Oncol., 4, 1025 (1994)) and in the urine of patients with squamous cell carcinomas of the head, neck, and lung (Witters et al., Clin. Cancer Res., 1, 551 (1995)). Ilekis et al. (Gynecol. Oncol., 65, 36 (1997)) have recently observed a positive association between levels of a p80 sErbB1 protein and full-length ErbB1 in tissue samples of serous cystadenocarcinomas of the ovary. In addition, ErbB1 receptors have been shown to be over-expressed in various human tumor cell lines and neoplasms (Xu et al., Proc. Nat'l. Acad. Sci, 81, 7308 (1984); Salomon et al., Crit. Rev. Oncol. Hematol., 19, 183 (1995)), including cancers of the breast (King et al., Science, 229, 974 (1985)), lung (Hendler et al., Proc. Am. Soc. Clin. Oncol., 8, 223 (1989); Veale et al., Cancer Res., 49, 1313 (1989)), brain (Schlegel et al., Int. J. Cancer, 56, 72 (1994)), bladder (Neal et al., Cancer, 65, 1619 (1990); Mellon et al., J. Urol., 153, 919 (1995)), and ovary (Berchuck et al., Am. J. Obstet. Gynecol., 164, 669 (1991); Scambia et al., J. Clin. Oncol., 10, 529 (1992)).

Thus, the current research concerning the biological role and function of EGF receptors has been contradictory, and does not provide a clear indication of how any particular EGF receptor can be used as a tool in diagnosing any particular cancer type. Therefore, a need exists for the isolation of soluble epidermal growth factor receptor protein molecules and their isoforms, and for the characterization of their correlated disease conditions. In addition, a useful, quantitative diagnostic method to detect the presence of biologically relevant, specific isoform expression in human body fluids and tissue for diagnosing the onset and progression of diseases associated with these soluble epidermal growth factor receptor protein molecules is also needed.

SUMMARY OF THE INVENTION

In a first aspect, the invention provides several novel isolated and purified non-genomic nucleic acids which encode soluble isoforms of the human EGFR/ErbB1, as well as nucleic acids encoding engineered variants of these proteins. Preferred embodiments of this aspect of the invention are nucleic acid sequences which specifically encode a soluble form of a human EGFR ("sEGFR/sErbB1") whose amino acid sequence comprises the sequence of SEQ ID NO:1. The nucleic acid embodiments of the invention include, e.g., DNA SEQ ID NO:2, which is the naturally occurring sequence encoding the polypeptide SEQ ID NO:1. The nucleic acids of the invention also include nucleic acid sequences which are complementary to or synonymous with SEQ ID NO: 2, (i.e., also encode DNA SEQ ID NO: 1.) Other preferred embodiments of this aspect of the invention include nucleic acids which encode proteins which comprise a sequence which has at least 90% identity with SEQ ID NO. 1, more preferably at least 95% identity with SEQ ID NO: 1, more preferably at least 98% identity with SEQ ID NO: 1, and most preferably at least 99% identity with SEQ ID NO. 1. A preferred embodiment of these nucleic acids would be a nucleic acid encoding the naturally occurring variant SEQ ID NO: 3, which is approximately 90.9% identical to SEQ ID NO: 1 (641 out of 705 amino acids). Other preferred embodiments of these nucleic acids include nucleic acids encoding the point-mutation proteins SEQ ID NO: 4, SEQ ID NO: 5, and SEQ ID NO: 6, which are approximately 99.8% identical to SEQ ID NO: 1 (704 out of 705 amino acids). Other embodiments of the nucleic acid sequence invention include nucleic acids which are complementary to the above nucleic acids.

The invention also provides an expression cassette comprising a nucleic acid of the invention encoding a sEGFR/sErbB 1, which is operably linked to a promoter functional in a host cell. Another aspect of the present invention is a method of producing sEGFR/sErbB1 polypeptides by incorporating such cassettes into expression vectors used to transform prokaryotic or eukaryotic host cells to express sEGFR/sErbB1 polypeptide. The sEGFR/sErbB1 polypeptide may then be isolated from the host cell or the culture media by methods well known in the protein purification arts. The vectors of the invention also may contain a functional DNA sequence that is comprised of a selectable marker gene and/or reporter gene, as described below, or an additional nucleic acid sequence encoding a polypeptide tag for purification. Another aspect of the present invention is an isolated and purified sEGFR/sErbB1, produced as above. A preferred sEGFR/sErbB1 comprises a polypeptide having SEQ ID NO:1. sEGFR/sErbB1 can be employed in cell growth assays, ligand binding assays, and biomarker detection assays such as those described in Examples below.

Yet another aspect of the present invention are polypeptides useful for generating antibodies specific to the proteins encoded by the amino acid sequences of the invention, including SEQ ID NO: 1, SEQ ID NO: 3, SEQ ID NO: 4, SEQ ID NO: 5, and SEQ ID NO: 6. The polypeptides of the invention comprise an amino acid sequence of 10 to 25 amino acids in length, more preferably 11 to 21 amino acids in length, and most preferably 14 to 20 amino acids in length, wherein the amino acid sequence is identical to an amino acid sequence of similar length in an amino acid sequence selected from the group consisting of: amino acids 628-705 of SEQ ID NO: 1, amino acids 628-705 of SEQ ID NO: 3, amino acids 628-705 of SEQ ID NO: 4, amino acids 628-705 of SEQ ID NO: 5, and amino acids 628-705 of SEQ ID NO: 6. Another aspect of the invention is an immunogenic conjugate comprising one of the above polypeptides and a carrier molecule. Preferred carrier molecules for use in immunogenic conjugates include keyhole limpet hemocyanin (KLH) and bovine serum albumin (BSA). Yet another aspect of the present invention are monoclonal or polyclonal antibodies produced using the above polypeptides which are specific for a protein selected from the group consisting of: SEQ ID NO: 1, SEQ ID NO: 3, SEQ ID NO: 4, SEQ ID NO: 5, and SEQ ID NO: 6; and which do not cross-react with other EGFR/ErbB1 isoforms.

Another aspect of the present invention is an expression cassette comprising: a preselected DNA segment that is complementary to SEQ ID NO:2 that is operably linked to a promoter functional in a host cell. Thus, the present invention provides an expression cassette that expresses an "antisense" mRNA transcript of a DNA sequence of the invention. Another aspect of the invention is a method of using this transcript by transforming a host cell with an expression cassette comprising the complementary sequence which is expressed within the host cell, and thus altering EGFR and/or sEGFR/sErbB1 expression, cell growth and/or differentiation of the host cell. In addition, such complementary transcripts may be utilized in RNAse protection assays to determine the level of cellular expression of mRNAs encoding SEQ ID NO: 1.

Yet another aspect of the invention is a sandwich immunoassay method for detecting or determining the concentration of soluble and full-length human epidermal growth factor receptor in a biological sample obtained from a patient. The method comprises: a) contacting an amount of a first purified antibody that specifically reacts with a first epitope of the extracellular ligand binding domain of sEGFR/sErbB1 with the patient biological sample to be tested, wherein the first purified antibody is modified with a first labeling moiety, b) contacting the sample with an amount of a second purified antibody that specifically reacts with a second epitope of sEGFR/sErbB1, wherein the second purified antibody is modified with a second labeling moiety, and wherein the second purified antibody does not competitively inhibit the binding of the first purified antibody, and c) determining presence or amount of the soluble epidermal growth factor receptor complexed with said antibodies by detecting the co-presence of the first and second labels. In preferred embodiments of this assay, the first antibody is either MAb R.1 or an antibody which binds to the same epitope as MAb R.1 (i.e. competitively inhibits the binding of MAb R.1 to the ligand binding domain of EGFR/ErbB1). In further preferred embodiments, the second antibody is MAb 528, or an antibody which binds to the same epitope as MAb 528 (i.e. competitively inhibits the binding of MAb 528 to the ligand binding domain of EGFR/ErbB1). In especially preferred embodiments, either the first or second labeling moiety is acridinium. In preferred embodiments of this aspect of the invention the patient biological sample is blood, serum, plasma, urine, saliva, sputum, breast nipple aspirates, or ascites fluid.

The invention further provides a diagnostic method for determining the presence, or risk, of an ovarian carcinoma in a female human patient. The method comprises a) determining the concentration of soluble EGFR/sErbB1 in a biological sample obtained from a female patient with ovarian cancer (e.g., by the above immunochemical method,) b) comparing the concentration obtained in a) with a normal or baseline level for soluble EGFR/sErbB1 that is preferably established with samples from female humans without ovarian cancer, and c) correlating a decrease in the concentration of sEGFR/sErbB1 in the patient's sample with the presence of an ovarian carcinoma in the patient. In further embodiments of the aspect of the invention, a female patient may be monitored with repeated testing to determine the onset or progression of ovarian cancer. In further embodiments, the female patient may be tested before and after radiation, chemotherapy, or surgical treatment to monitor the regression or progression of ovarian cancer.

Yet another aspect of the invention is a method to increase or decrease the half-life of EGFR/ErbB1 ligands in the circulatory system of a human patient. For example, the method may be used to increase the circulatory half-life of ligands, such as EGF and TGF-α by binding to the ligands in the patient's blood, thereby inhibiting ligand degradation and extending the half-life of these ligands in the patient. Alternatively, the method may be used to decrease the circulatory half-life of these ligands by allowing cells to remove sEGFR/sErbB1-ligand complexes from the circulation by endocytosis and intravellular membrane support. The method comprises administering to a human patient a ligand-half-life-altering amount of a sEGFR/sErbB1 protein with an amino acid sequence chosen from the group consisting of SEQ ID NO: 1, SEQ ID NO: 3, SEQ ID NO: 4, SEQ ID NO: 5, and SEQ ID NO: 6.

Yet another embodiment of the invention is a method to regulate cellular proliferation and cellular differentiation. The sEGFR/sErbB1 molecules inhibit cytokines and receptors necessary for normal cell proliferation and differentiation and may play important roles in regulating development, wound healing, carcinogenesis, and tumor progression. The method comprises administering to a cell a cytokine-function-inhibiting amount of a sEGFR/sErbB1 protein with an amino acid sequence chosen from the group consisting of SEQ ID NO: 1, SEQ ID NO: 3, SEQ ID NO: 4, SEQ ID NO: 5, and SEQ ID NO: 6.

Yet another embodiment of the invention is a diagnostic kit package for detecting or determining sEGFR/sErbB1 in a human biological sample. The kit comprises: (a) a solid phase capable of having attached thereto a first antibody; (b) a first antibody that binds to a first epitope on the extracellular ligand binding domain of the human epidermal growth factor receptor, wherein the first antibody is modified with an attachment label moiety; (c) a second antibody which specifically binds to a second epitope on the extracellular ligand binding domain of the human epidermal growth factor receptor, wherein the second antibody is labeled with a second label moiety; and (d) instructions for carrying out the immunoassay of the invention. Preferred kits comprise antibodies specific to a protein having the amino acid sequence SEQ ID NO: 1, SEQ ID NO: 3, SEQ ID NO: 4, SEQ ID NO: 5, or SEQ ID NO:6.

BRIEF DESCRIPTION OF THE FIGURES AND DEFINITIONS

FIG. 1. Schematic representation of full-length, p60 sEGFR, and normal p110 EGFR transcripts. Open boxes represent exons. Lines represent introns.

Figure 2:
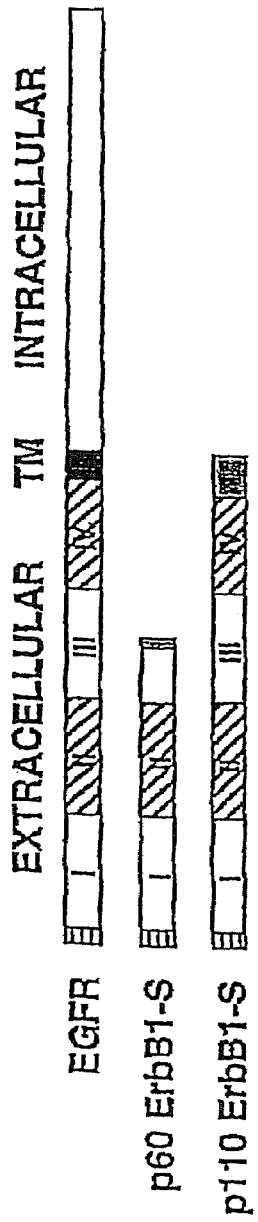

FIG. 2. Structural comparison of p60 and p110 soluble isoforms of EGFR relative to the full-length EGFR.

FIG. 3. Schematic representation of alternative exons located in human EGFR introns 15 and 16.

FIG. 4. DNA and translated protein sequences (FIGS. 4A and 4B; SEQ ED NOs: 21-54).

Figure 5:
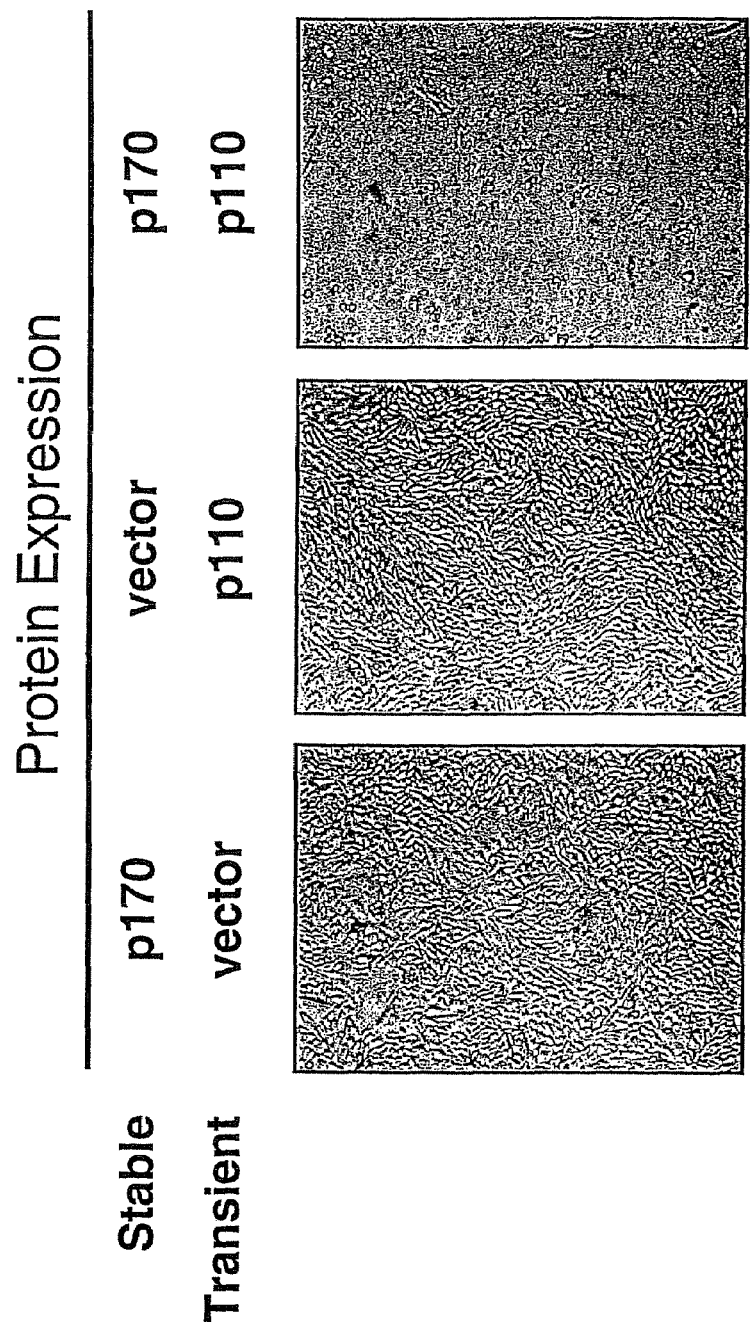

FIG. 5. Diagram showing the effects of sEGFR/sErbB1 protein isoform in vitro. Chinese hamster ovary (CHO) cells were transfected with either the full-length human EGFR cDNA (encoding p170 EGFR) in the expression vector pcDNA3 (Invitrogen) or with the vector alone. Stable clonal isolates were selected with G418 and these cells were then transiently transfected with the alternative 3.0 kb EGFR cDNA (encoding p110 sErbB1) or with vector alone. When p170 EGFR and sEGFR/sErbB1 were co-expressed in the same cells, significant cell death was observed 24-48 hours following transfection; however, no cell death was observed when either of these proteins was expressed individually.

Figure 6:
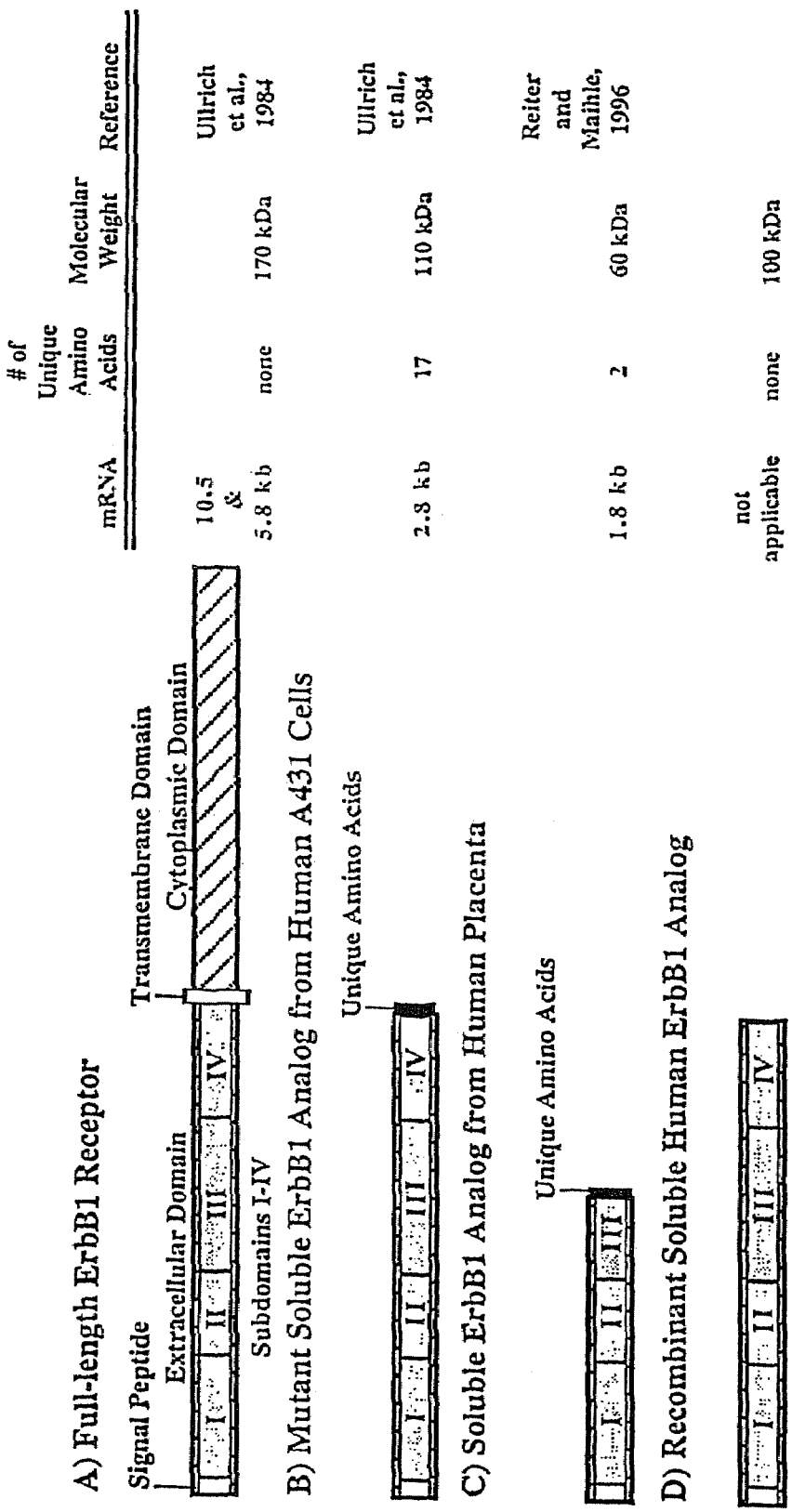

FIG. 6. This diagram illustrates the structure of several EGFR isoforms, including the full-length EGF receptor, p170 ErbB1 (A), the mutant p110 soluble ErbB1 analog from A431 cells [which differs in sequence from normal p110 from human placenta, as described below] (B), the p60 soluble ErbB1 analog of human placenta (C), and a recombinant p100 soluble ErbB1 analog (D). Additional information about these molecules is given in the chart. The full-length 170 kD ErbB1 receptor contains an extracellular domain with four distinct subdomains (I-IV), a transmembrane domain, and a cytoplasmic domain. The mutant A431 p110 sErbB1 analog contains extracellular subdomains I through IV and 17 unique amino acids at its carboxy-terminal end. The p60 sErbB1 analog contains subdomains I and II, a portion of subdomain III, and 2 unique carboxy-terminal amino acids. Recombinant human p100 sErbB1 ends at amino acid 589 (nucleotide numbering according to Ullrich et al., 1984) and, therefore, embodies subdomains I through IV without any additional unique carboxy-terminal amino acids. The mutant p110 and 'natural' p60 human sErbB1 analogs are synthesized from alternatively spliced.2.8 kb and 1.8 kb mRNA transcripts of A431 carcinoma cells and normal placenta, respectively. QT6 cells transfected with the plasmid vector, psErbB1ECD589, synthesize the recombinant human p100 sErbB1 analog. The p110 sEGFR/sErbB1 isoform encoded by the nucleic acids of the invention, not shown, contains subdomains I-IV, as well as its 78 unique amino acid carboxy end sequence.

FIG. 7. Dose-response curves of the ALISA toward whole cell lysates (A) and conditioned culture media (B) from various cell lines that synthesize different combinations of ErbB-related molecules are shown (bottom axes). The standard dose-response curve with p170 ErbB1 also is shown on each graph (top axes). QT6 quail fibroblasts do not synthesize any human ErbB molecules. The human breast carcinoma cell line, MDA-MB-453, is known to synthesize full-length ErbB2, ErbB3, and ErbB4, but not ErbB1. The human breast carcinoma cell line, SK-BR-3, is known to synthesize complete ErbB1, ErbB2, ErbB3, and ErbB4 receptors. The dose-response curves with A431 and SK-BR-3 whole cell lysates are positive, and those with MDA-MB-453 and QT6 whole cell lysates are negative (A). A431 cells secrete a mutant p110 sErbB1 analog; whereas QT6, QT6/pDR161, and QT6/psErbB1ECD589 cells secrete no ErbB1-related molecules, p60 sErbB1, and p100 sErbB1, respectively. MDA-MB-453 and SK-BR-3 cells are not known to secrete sErbB1 molecules. However, SK-BR-3 cells have been shown to secrete a sErbB2 analog of approximately 105 kD. The dose-response curves with A431 and Qt6/psErbB1ECD589 conditioned media are positive, and those with Qt6/pDR161 and SK-BR-3 conditioned media are negative (13). Thus, as is shown by these graphs, the ALISA described in Example V detects ErbB1 isoforms which contain subdomains I-IV (A431 p110, p100, p170, and p110 sEGFR/sErbB1), but does not detect isoforms which contain only sub domains I-III.

Figure 8:
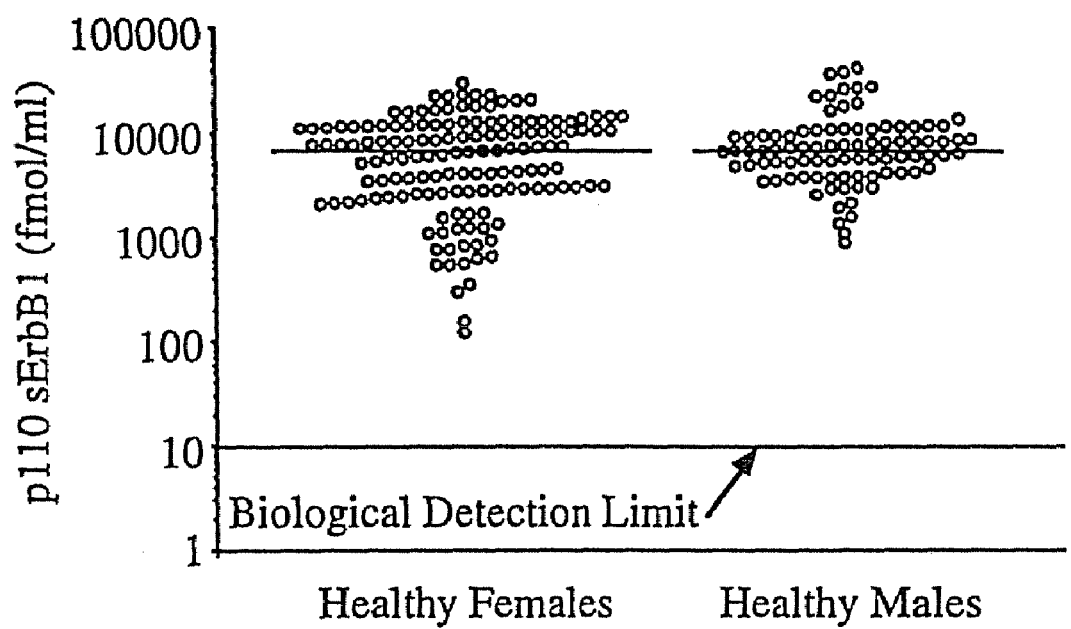

FIG. 8. The concentration of sErbB1 in normal human female (n=144) and male (n=88) sera as measured by the ALISA of Example V are compared as described in Example VI.

Figure 9:
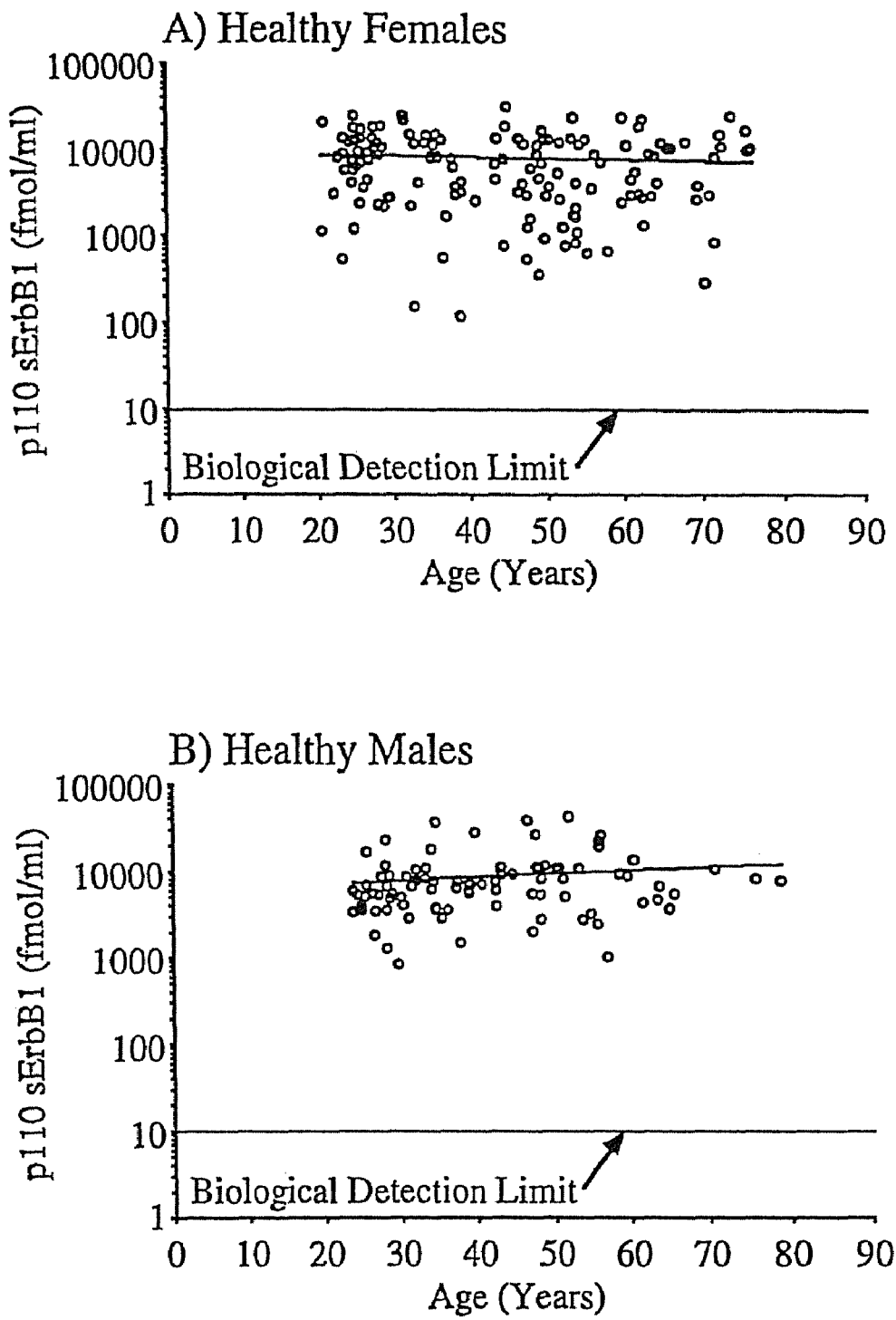

FIG. 9. The serum sErbB1 concentrations for healthy females (A) and healthy males (B) are plotted as a function of patient age.

Figure 10:
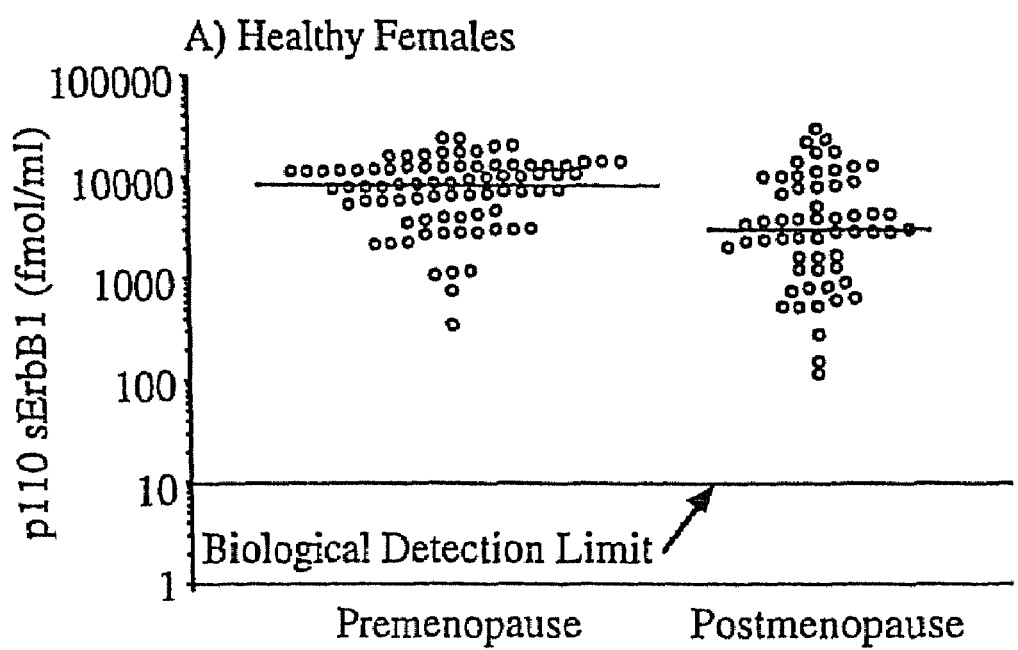

FIG. 10. The serum sErbB1 concentrations of the healthy females are plotted as a function of pre- or post-menopause status.

Figure 11:
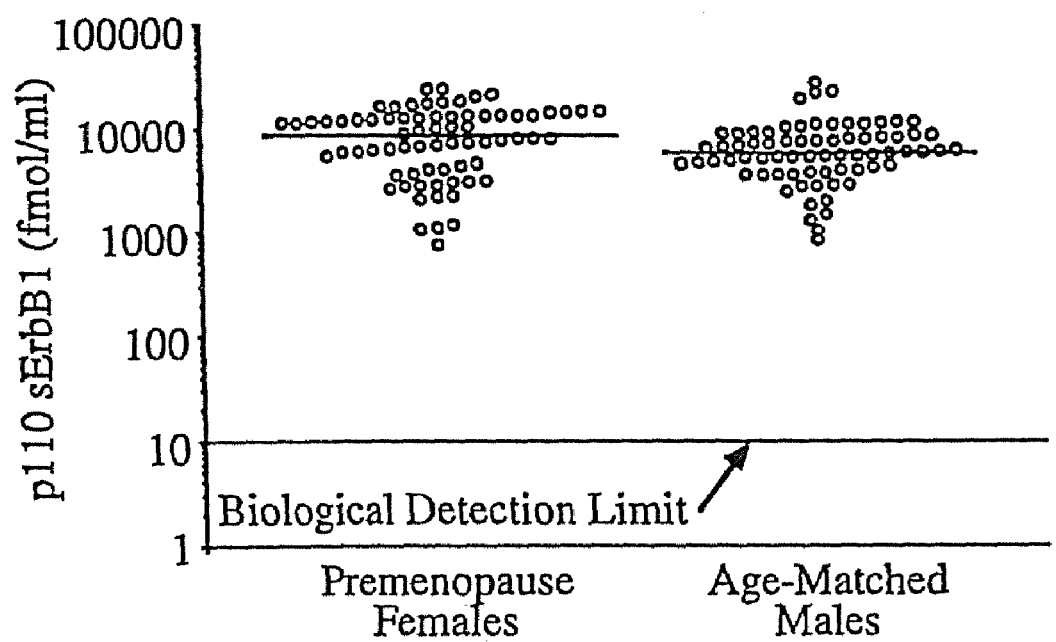

FIG. 11. The serum sErbB1 concentrations of pre-menopausal females are plotted with an age-matched group of males.

FIG. 12. The serum sErbB1 concentrations, measured using the ALISA of Example V, of healthy women in a control group, with pre-operative epithelial ovarian cancer (EOC), with benign ovarian tumors, and with benign gynecological diseases are shown. The median sErbB1 concentration of women with EOC is significantly less than that of women without ovarian cancers.

Figure 13:
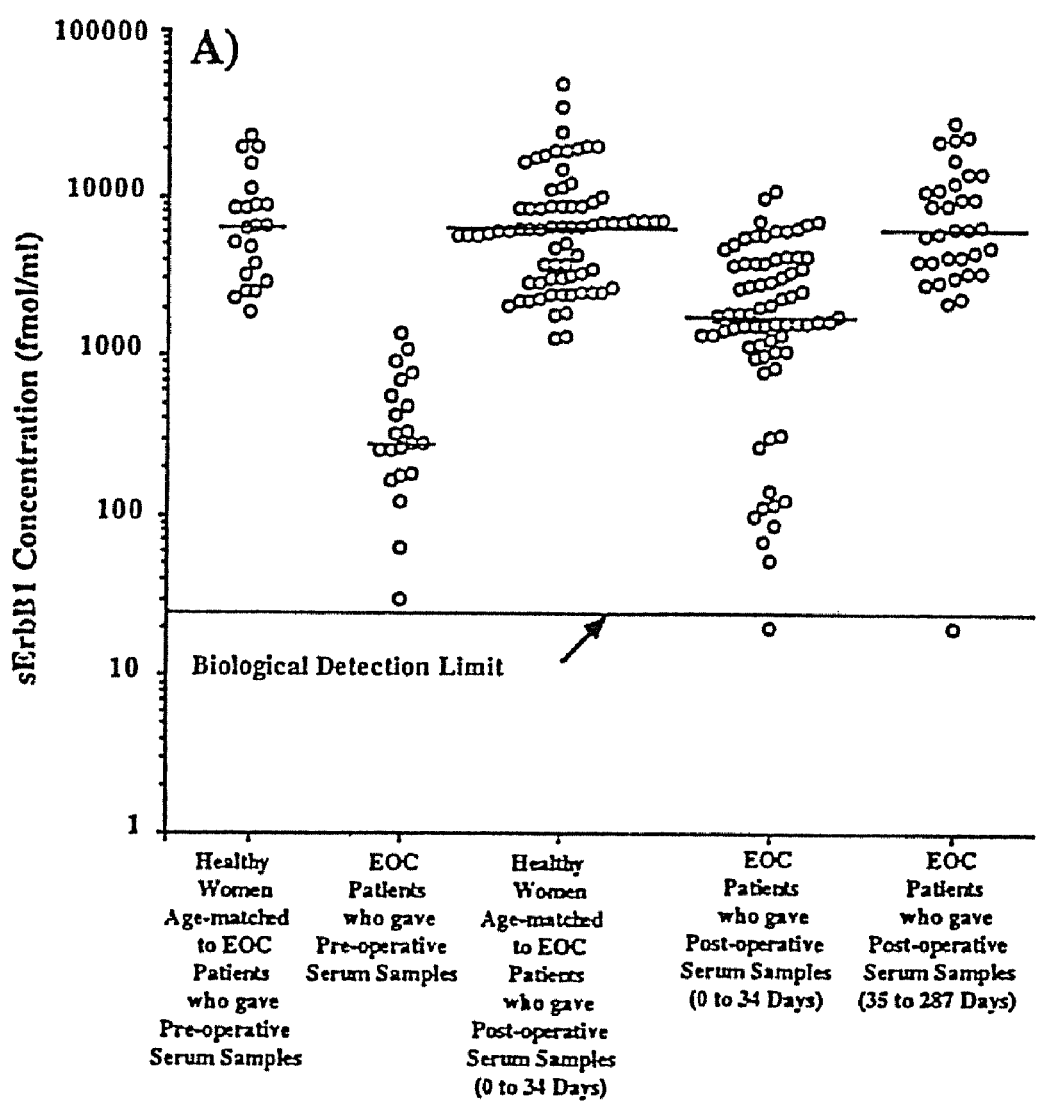

FIG. 13. The serum sErbB1 concentrations, measured using the ALISA of Example V, of healthy women in a control group age-matched to the pre-operative EOC group, EOC patients who gave pre-operative samples, a control group age-matched to the post-operative EOC group, a post-operative EOC group 0-34 days after surgery, and a post-operative EOC group 35-287 days after surgery.

Figure 14:
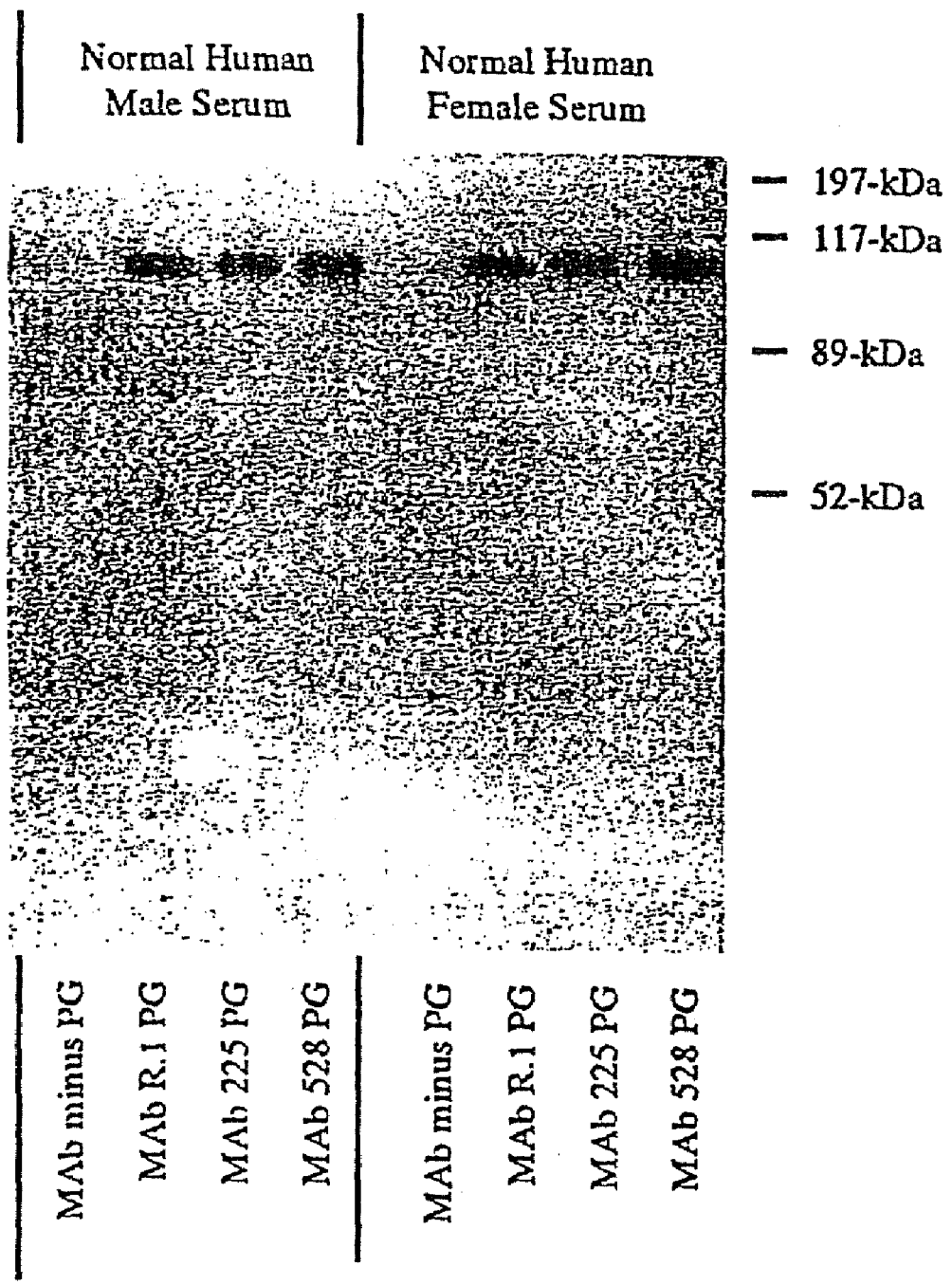

FIG. 14. Normal human male and female sera were immunoprecipitated with Protein-G MAb minus, R.1-, 225-, or 528-coupled resins and Western blotted with a mixture (15E11, 2D2, LA22, and C11) of anti-ErbB1 ECD-specific MAbs. A reactive band of approximately 110 kD eluted from each MAb affinity resin, but not from the MAb minus resin used to immunoprecipitate normal male or female sera.

Figure 15:
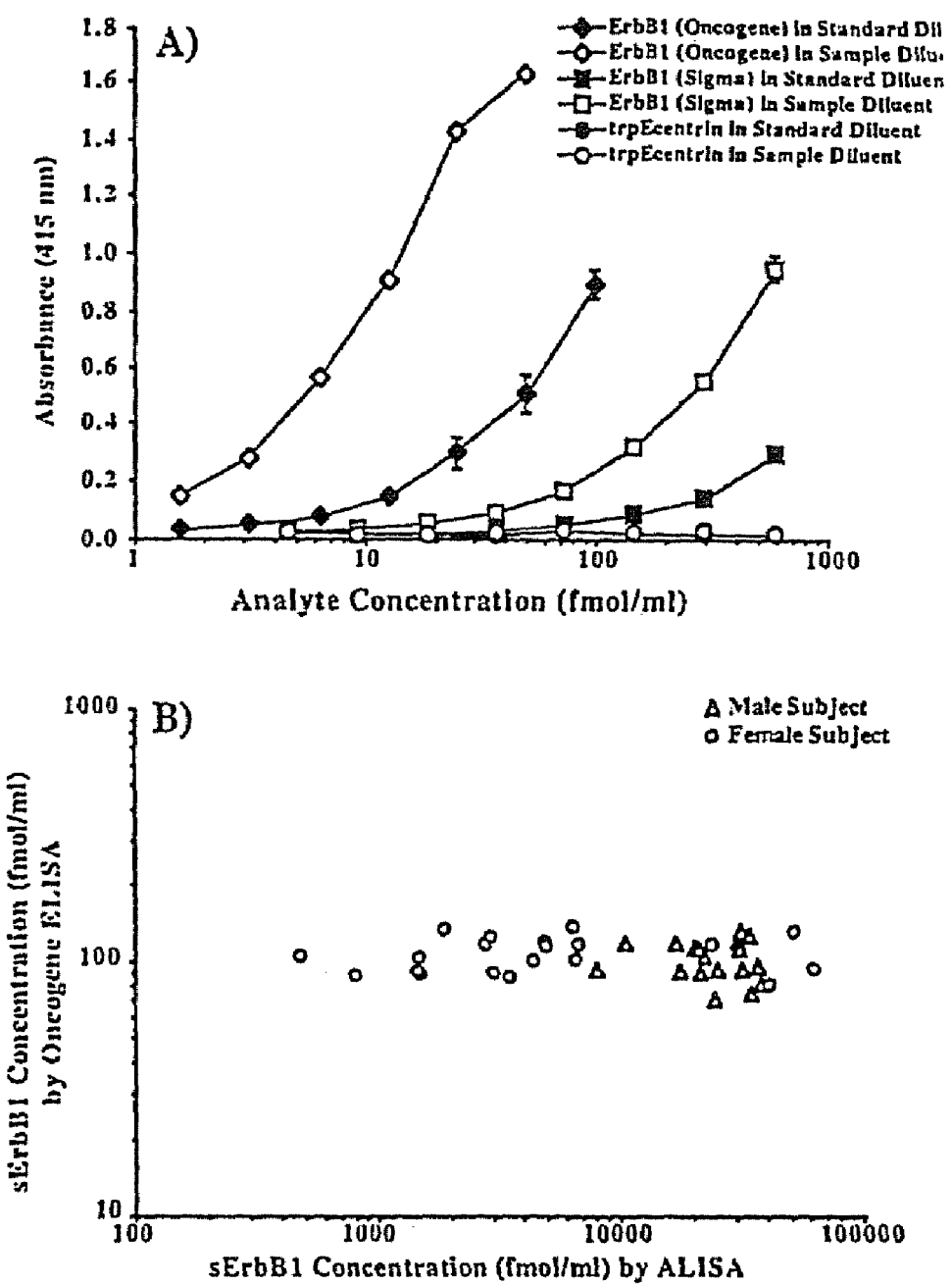

FIG. 15. This figure shows the dose-response curves of the current Oncogene Research Products ELISA with the p170 ErbB1 standard supplied in the Oncogene Research Products kit and with the p170 ErbB1 standard, purchased from Sigma (A). Serial dilutions of both p170 ErbB1 standards and the zero calibrator, trpEcentrin, were prepared and assayed in both standard and sample diluents. Both standards show stronger dose-response curves in the sample diluent than the standard diluent. In addition, the p170 ErbB1 standard supplied by Oncogene Research Products gives stronger response curves than the p170 ErbB1 standard purchased from Sigma Chemical. Serum sErbB1 levels measured with the Oncogene Research Products ELISA for forty healthy human subjects (20 women and 20 men) are compared to the sErbB1 levels measured with our ErbB1 ECD-specific ALISA (B). The sErbB1 levels determined with the Oncogene Research Products ELISA for men are not significantly different from those of women. No association between the sErbB1 values obtained with the Oncogene Research Products ELISA and those obtained with the ErbB1 ECD-specific ALISA is observed.

DEFINITIONS

As used herein, the term "soluble" epidermal growth factor receptor (sEGFR or sErbB1) means that the epidermal growth factor receptor polypeptide is found in a form that does not harbor a transmembrane domain, i.e., a portion of the sEGFR/sErbB1 is not found physically embedded in the lipid bilayer which comprises the cell membrane in the cell of its origin through a constituent peptide domain. However, sEGFR/sErbB1 may be embedded or attached to the cell membrane through other moieties such as lipids, carbohydrates, and/or proteins. Preferred soluble isoforms of the receptor are secreted by the cell, proteolytically cleaved from the cell surface or released from the cell surface by other mechanisms. Other preferred soluble isoforms of the receptor may comprise the extracellular ligand binding domain of the sEGFR/sErbB1, and lack at least a portion of the transmembrane domain (TM), i.e., the membrane-anchoring domain of the EGFR, so as to result in an EGFR which is not firmly anchored to, attached to, or embedded in the cell membrane.

As used herein, the terms "isolated and/or purified" refer to in vitro isolation of a nucleic acid or polypeptide molecule from its natural or transformed cellular environment, and from association with other naturally occurring components of the cell. Such molecules may then be sequenced, replicated, manipulated, and/or recombined for artificial in vivo or in vitro expression. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

As used herein, the term "biological activity" of a peptide of the invention is defined to mean a polypeptide comprising a subunit of a peptide having SEQ ID NO:1, or a variant thereof, which has at least about 10%, preferably at least about 50%, and more preferably at least about 90%, of the activity of a peptide having SEQ ID NO:1. The activity of a peptide of the invention can be measured by methods well known in the art including, but not limited to, the ability to bind EGF, or the ability of the peptide to elicit a sequence-specific immune response when the peptide is administered to an organism, e.g., goat, sheep or mouse.

As used herein with regard to polypeptide sequences, the term "% identity" means the percentage of amino acids in a compared sequence which are identical with the amino acids in a reference sequence, when both sequences are aligned and gaps are introduced, when necessary, to produce the best match. As used herein, sequences with "substantial identity" are at least 90% identical. It is also preferred that the non-identical amino acids in the compared sequence be conservatively substituted with like amino acids in substantially identical polypeptides.

As used herein, the term "complementary," when used to describe nucleic acids, refers to the ability of the nucleic acids to hybridize with each other. Preferred complementary nucleic acids have an exact complementarity with regard to A/T and G/C matching. However, substantially complementary nucleic acids which hybridize to RNA or DNA and remain stably bound under stringent conditions, as defined by methods well known in the art (Sambrook et al., supra), would be sufficiently complementary for some uses (e.g., as antisense nucleotide sequences.)

As used herein, the term "synonymous," when used to describe nucleic acids, refers to the polypeptide sequence encoded by a compared nucleic acid relative to a reference nucleic acid. The genetic code is well known by those of skill in the art, and sequences with codon substitutions which encode the same amino acid can be easily devised for various purposes (e.g., introducing convenient restriction enzyme cleavage sites or optimizing codon usage for a particular recombinant protein production organism) without changing the translated polypeptide sequence. Utilizing common tools such as phosphoramidite polynucleotide synthesis and site directed mutagenesis or other recombinant techniques, such substitutions may easily be effected by those of ordinary skill in the art. Thus, sequences which are synonymous with the exemplary nucleotide sequences are also considered to be within the scope of the present invention. However, sequences which do not directly encode the translation of the same protein would not be considered to be "synonymous." Specifically, the full genomic EGFR/ERBB1/HER1 gene is not considered to be synonymous with the nucleic acids of the invention, as the full-length gene can encode many alternatively spliced transcripts, including the nucleic acids of the invention, but the full-length transcript does not directly encode proteins such as SEQ ID NO: 1.

The terms "recombinant nucleic acid" or "preselected nucleic acid," e.g., "recombinant DNA sequence or segment" or "preselected DNA sequence or segment" refer to a nucleic acid that has been derived or isolated from any appropriate tissue source and that may be subsequently chemically altered, typically in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

"Regulatory sequences" is defined to mean RNA or DNA sequences necessary for the expression, post-transcriptional modification, translation, and post-translational modification of an operably linked coding sequence in a particular host organism. The control sequences that are suitable for prokaryotic cells, for example, include a promoter, and optionally an operator sequence, and a ribosome binding site. Eukaryotic cells are known to utilize promoters, stop sequences, enhancers, splicing, and polyadenylation signal sequences, as well as glycosylation and secretory signal sequences.

"Operably linked" is defined to mean that nucleic acids are placed in a functional relationship with one another in a nucleic acid sequence. For example, DNA for a secretory leader is operably linked to DNA for a polypeptide if it is expressed as a pro-polypeptide that participates in the secretion of the polypeptide; a promoter or enhancer is operably linked to a coding sequence if it affects the transcription of the sequence; or a ribosome binding site is operably linked to a coding sequence if it is positioned to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, the synthetic oligonucleotide linkers or mutagenesis are used in accord with conventional practice.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including avian, plant, insect, yeast, fungal or bacterial sources. Generally, the preselected DNA sequence is related to a DNA sequence that is resident in the genome of the host cell but is not expressed, or not highly expressed, or, alternatively, over-expressed.

The terms "transfected" or "transformed" are used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding sEGFR/sErbB1, which the host cell may or may not express significant levels of autologous or "native" sEGFR/sErbB1.

DETAILED DESCRIPTION OF THE INVENTION

In order to more fully understand the mechanism by which the sEGFR/sErbB1 influences cell growth and differentiation in normal tissue, cDNAs which encode the extracellular ligand binding domain, but not the cytoplasmic kinase domain, of the human epidermal growth factor receptor were isolated from a human placental cDNA library. Besides identifying a soluble form of the human epidermal growth factor receptor which may play a role in, or be associated with, cell growth and differentiation in normal cells, the identification and isolation of cDNAs encoding novel sEGFR/sErbB1 transcripts has proven useful for defining the molecular basis for some neoplastic processes. Applicants have utilized monoclonal antibodies against the extracellular domain of EGFR to produce a useful diagnostic test which demonstrates the correlation between the discovered forms of sEGFR/sErbB1 and ovarian cancer. By further utilizing the nucleic acid sequences of the invention to recombinantly produce the encoded sEGFRs/sErbB1s, or producing specific antibodies to the unique carboxy terminal sequence of these proteins, other important advances in therapeutics and diagnostics may be realized through the invention.

Applicants have demonstrated a significant correlation between the levels of sEGFR/sErbB1 and ovarian cancer. Thus, patient samples, e.g., tissue biopsies, sera or plasma, may now be analyzed with antibodies specific for the sEGFR/sErbB1 to detect the presence and progression of ovarian carcinomas in patients. As demonstrated by the examples below, applicants have found the level of sEGFR/sErbB1 in patient samples to be useful in determining residual disease, responsiveness to chemotherapy, or overall survival. In addition, the levels of particular isotypes of sEGFR/sErbB1 in a patient may be a useful indicator of the stage, grade, histological and molecular subtype of a tumor.

Furthermore, the cloning of transcripts encoding sEGFRs/sErbB1s will elucidate the molecular mechanism giving rise to the presence or absence of sEGFR/sErbB1 in patients with disease. Once the molecular mechanism underlying the expression of sEGFR/sErbB1 is understood, molecular genetic based therapies directed to controlling the expression of sEGFR/sErbB1 can then be employed to correct, inhibit or supplement the expression of sEGFR/sErbB1 or full-length EGFR in patients with the disease. For example, an expression vector containing cDNA encoding antisense sEGFR/sErbB1 transcripts can be introduced into tumor cells to inhibit or reduce the overexpression of full-length EGFR.

The cDNAs encoding sEGFR/sErbB1 also can be employed in expression cassettes to synthesize sEGFR/sErbB1 in vitro. In vitro prepared sEGFR/sErbB1 can be employed to obtain antibodies specific for soluble forms of the EGFR. In vitro synthesized sEGFR/sErbB1 may also be employed in a pharmaceutical formulation which, when administered to a human, can form heterodimers with full-length ErbB family members to block receptor activation, compete with the full-length ErbB receptors for ligand, or block EGFR signal transduction post-ligand binding, and thus suppress or decrease the growth stimulatory and other signaling activities of ErbB receptor tyrosine kinases.

The cDNAs of the present invention are useful for detecting the expression of sEGFR/sErbB1, for detecting related DNA molecules and for amplifying nucleic acid sequences, wherein said sequences fall within the scope of the present invention. The antibodies of the invention, besides being useful to detect sEGFR/sErbB1 levels in patient samples, maybe useful in vivo to inhibit the natural functions of sEGFR/sErbB1 in various disease states.

Sources and Isolation of Nucleic Acids Encoding sEGFR/sErbB1

Sources of nucleotide sequences from which the present cDNA molecules encoding human sEGFR/sErbB1 can be derived include total or polyA$^+$RNA from any human cellular source, preferably from embryonic cells such as those from placental tissue, carcinomas, or cell lines derived therefrom, from which cDNAs encoding sEGFR/sErbB1 can be derived by methods known in the art and described below in Example I. Other sources of the DNA molecules of the invention include cDNA libraries derived from any human cellular source including placental cDNA libraries.

A nucleic acid molecule encoding sEGFR/sErbB1 can be identified and isolated using standard methods, as described by Sambrook et al., Molecular Cloning: A Laboratory Manual, Cold Spring Harbor, N.Y. (1989). For example, reverse transcriptase PCR(RT-PCR) can be employed to isolate and clone sEGFR/sErbB1 cDNAs.

Oligo-dT can be employed as a primer in a reverse transcriptase reaction to prepare first-strand cDNAs from isolated RNA that contains RNA sequences of interest, e.g., total RNA isolated from human placental tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

Primers are made to correspond to highly conserved regions of polypeptides or nucleotide sequences which were identified and compared to generate the primers, e.g., by a sequence comparison of other mammalian or avian EGFRs, particularly sEGFR/sErbB1s. One primer is prepared which is predicted to anneal to the antisense strand, and another primer prepared which is predicted to anneal to the sense strand, of a DNA molecule that encodes a soluble isoform of the human EGFR.

The products of each PCR reaction are separated by an agarose gel and all consistently amplified products are gel purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs that encode sEGFR/sErbB1 is to screen a cDNA library generated from embryonic tissue. Screening for DNA fragments that encode all or a portion of a cDNA encoding sEGFR/sErbB1 can be accomplished by probing the library with a probe, which has sequences that are highly conserved between genes believed to be related to sEGFR/sErbB1, e.g., DNA encoding rat or avian sEGFR/sErbB1 or encoding sEGFR/sErbB1 from A431 cells, or by screening of plaques for binding to antibodies that specifically recognize sEGFR/sErbB1. DNA fragments that bind to a probe having sequences which are related to sEGFR/sErbB1, or which are immunoreactive with antibodies to sEGFR/sErbB1 can be subcloned into a suitable vector and sequenced and/or used as probes to identify other cDNAs encoding all or a portion of sEGFR/sErbB1.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA (Lawn et al., Nucleic Acids Res., 9, 6103 (1981); Goeddel et al., Nucleic Acids Res., 8, 4057 (1980)).

Variants of the DNA Molecules of the Invention

Nucleic acid molecules encoding amino acid sequence variants of sEGFR/sErbB1 are prepared by a variety of methods known in the art. These methods include, but are not limited to, isolation from a natural source (in the case of naturally occurring amino acid sequence variants such as SEQ ID NO: 3-6) or preparation by oligonucleotide-mediated (or site-directed) mutagenesis, PCR mutagenesis, and cassette mutagenesis of an earlier prepared variant or a non-variant version of sEGFR/sErbB1 polypeptide.

Oligonucleotide mediated mutagenesis is a preferred method for preparing amino acid substitution variants of sEGFR/sErbB1. This technique is well known in the art (Adelman et al., DNA, 2, 183 (1983)). Briefly, sEGFR/sErbB1 DNA is altered by hybridizing an oligonucleotide encoding the desired mutation to a DNA template, where the template is the single-stranded form of a plasmid or bacteriophage containing the unaltered or native DNA sequence of sEGFR/sErbB1. After hybridization, a DNA polymerase is used to synthesize an entire second complementary strand of the template that will thus incorporate the oligonucleotide primer, and will code for the selected alteration in the sEGFR/sErbB1 DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art (Crea et al., Proc. Nat'l. Acad. Sci., 75, 5765 (1978)).

The DNA template can be generated by those vectors that are either derived from bacteriophage M13 vectors (the commercially available M13 mp 18 and M13 mp 19 vectors are suitable), or those vectors that contain a single-stranded phage origin of replication as described by Viera et al., Meth. Enzymol., 153, 3 (1987). Thus, the DNA that is to be mutated may be inserted into one of these vectors to generate single-stranded template. Production of the single-stranded template is described in Sections 4.21-4.41 of Sambrook et al., Molecular Cloning Laboratory Manual (Cold Spring Harbor Laboratory Press, N.Y. (1989)). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the sEGFR/sErbB1, and the other strand (the original template) encodes the native, unaltered sequence of the sEGFR/sErbB1. This heteroduplex molecule is then transformed into a suitable host cell, usually a prokaryote such as E. coli. JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotide triphosphates, deoxyriboadenosine (dATP), deoxyriboguanosine (dGTP), and deoxyribothymidine (dTTP), is combined with a modified thiodeoxyribocytosine called dCTP-(aS) (Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

A preferred embodiment of the invention is an isolated and purified DNA molecule comprising a preselected DNA sequence encoding a sEGFR/sErbB1 polypeptide comprising SEQ ID NO:2 having nucleotide substitutions which are "silent." That is, when nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO:2 at the first codon in the mature polypeptide (CTG in SEQ ID NO:2) includes the substitution of CTT, CTC or CTA for CTG. Nucleotide substitutions can be introduced into DNA segments by methods well known to the art (Sambrook et al., supra).

Chimeric Expression Cassettes

The recombinant or preselected DNA sequence or segment used to prepare expression cassettes for transformation, may be circular or linear, double-stranded or single-stranded. Generally, the preselected DNA sequence or segment is in the form of chimeric DNA, such as plasmid DNA that can also contain coding regions flanked by control sequences that promote the expression of the preselected DNA present in the resultant cell line. Aside from preselected DNA sequences that serve as transcription units for sEGFR/sErbB1 or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention. A preferred promoter useful in the practice of the invention is the CMV promoter. Another preferred promoter useful in the practice of the invention is the Rous Sarcoma Virus LTR promoter.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell. The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like (Lundquist et al. (U.S. Pat. No. 5,848,956)).

Reporter genes are used for identifying potentially transformed cells and for evaluating the functionality of regulatory sequences. Reporter genes that encode for easily assayable polypeptides are well known in the art. In general, a reporter gene is a gene which is not present in or expressed by the recipient organism or tissue and which encodes a polypeptide whose expression is manifested by some easily detectable property, e.g., enzymatic activity. Preferred genes include the chloramphenicol acetyl transferase gene (cat) from Tn9 of E. coli., the beta-glucuronidase gene (gus) of the uidA locus of E. coli, and the luciferase gene from firefly Photinus pyralis. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein (Sambrook et al., supra).

Transformation into Host Cells

The recombinant DNA can be readily introduced into host cells, e.g., mammalian, bacterial, yeast or insect cells by transfection with an expression vector comprising DNA encoding sEGFR/sErbB1 by any procedure useful for the introduction into a particular cell, e.g., calcium phosphate precipitation, lipofection, electroporation, and the like, to yield a transformed cell having the cDNA stably integrated into its genome, so that the DNA molecules, sequences, or segments, of the present invention are expressed by the host cell. That is, the present invention also provides a transformed host cell having a genome augmented by a recombinant (non-native) DNA sequence, preferably by a chromosomally integrated recombinant (genetically engineered) DNA sequence that includes a gene encoding a sEGFR/sErbB1.

sEGFR/sErbB1 Polypeptides

The present invention provides an isolated, purified sEGFR/sErbB1 polypeptide, which can be prepared by recombinant DNA methodologies. The general methods for isolating and purifying a recombinantly expressed protein from a host cell are well known to those in the art (Sambrook et al., supra). Moreover, since the present invention provides the complete amino acid sequence of sEGFR/sErbB1 (SEQ ID NO:1), sEGFR/sErbB1 or bioactive variants thereof can also be synthesized by the solid phase peptide synthetic method (Stewart et al., Solid Phase Peptide Synthesis, W.H. Freeman Co., San Francisco (1969); Merrifield, J. Am. Chem. Soc., 85, 2149 (1963); Meienhofer, "Hormonal Proteins and Peptides," ed.).

sEGFR/sErbB1 polypeptide expressed in a recombinant cell is purified from recombinant cell proteins or cellular polypeptides to obtain preparations that are substantially homogenous. For example, the culture medium or lysate can be centrifuged to remove particulate cell debris. The membrane and soluble protein fractions are then separated. sEGFR/sErbB1 polypeptide can then be purified from contaminant soluble or membrane proteins and polypeptides by fractionation on immunoaffinity or ion exchange columns; ethanol precipitation; reverse phase HPLC; chromatography on silica or on an anion exchange resin such as DEAF; chromatofocusing; SDS-PAGE; ammonium sulfate precipitation; gel filtration using, e.g., Sephadex G-75; or ligand affinity chromatography, and the like. An example of such purification is provided in Ilekis et al., supra, as well as in Example II herein.

sEGFR/sErbB1 polypeptide, variant sEGFR/sErbB1 polypeptides or biologically active subunits thereof can also be prepared by in vitro transcription and translation reactions. A sEGFR/sErbB1 expression cassette can be employed to generate sEGFR/sErbB1 transcripts that are subsequently translated in vitro so as to result in a preparation of substantially homogenous sEGFR/sErbB1, variant sEGFR/sErbB1, or biologically active subunits thereof. The construction of vectors for use in vitro transcription/translation reactions, as well as the methodologies for such reactions, are well known to the art.

Once isolated from the resulting transgenic host cells or from in vitro transcription/translation reactions, derivatives and chemically derived variants of the sEGFR/sErbB1 polypeptide can be readily prepared. For example, amides of the sEGFR/sErbB1 polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the sEGFR/sErbB1 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. In addition, the internal sEGFR/sErbB1 amino acid sequence of SEQ ID NO:1 can be modified by substituting one or two conservative amino acid substitutions for the positions specified, including substitutions that utilize the D rather than L form.

The invention also is directed to variant or modified forms of the sEGFR/sErbB1 polypeptide. One or more of the residues of this polypeptide can be altered, so long as the variant polypeptide has at least about 50%, preferably at least about 80%, and more preferably at least about 90%, of the biological activity of the polypeptide having SEQ ID NO:1. Conservative amino acid substitutions are preferred—that is, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

sEGFR/sErbB1 Variant Polypeptides

It is envisioned that variant sEGFR/sErbB1 polypeptides have at least one amino acid substitution relative to SEQ ID NO:1. In particular, amino acids are substituted in a relatively conservative manner. Such conservative substitutions are shown in Table I under the heading of exemplary substitutions. More preferred substitutions are under the heading of preferred substitutions. After the substitutions are introduced, the products are screened for biological activity.

TABLE I

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | Glu | glu |
| Cys (C) | Ser | ser |
| Gln (Q) | Asn | asn |
| Glu (E) | Asp | asp |
| Gly (G) | Pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | Giy | gly |
| Ser (S) | Thr | thr |
| Thr (T) | Ser | ser |
| Trp (W) | Tyr | tyr |
| Tyr (Y) | trp; phe; thr; ser | phe |
| Val (V) | ile; leu; met; phe; ala; leu norleucine | |

Amino acid substitutions falling within the scope of the invention, are, in general, accomplished by selecting substitutions that do not differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

It is preferred that the non-identical amino acids of engineered versions of these embodiments be conservatively substituted relative to the amino acids of SEQ ID NO. 1. It is also preferred that the proteins of the invention have at least 10% of the biological activity of the polypeptide SEQ. ID NO. 1, more preferably at least 50% of the biological activity of the polypeptide SEQ. ID NO. 1, and most preferably at least 90% of the biological activity of the polypeptide SEQ. ID NO. 1. The activity of the sEGFR/sErbB1 polypeptides of the invention can be measured by methods well known to the art including, but not limited to, ligand binding assays (Flickinger et al., Mol. Cell. Biol., 12, 883 (1992)), the ability of the sEGFR/sErbB1 to be bound by antibodies specific for the extracellular ligand binding domain of EGFR (see Example V, Maihle et al., supra, and Ilekis et al., supra), the ability of the sEGFR/sErbB1 to inhibit the kinase activity of the full-length EGFR, and growth inhibition assays (see Example III). Amino acid substitutions are introduced into the DNA molecules of the invention by methods well known to the art. For example, see the description herein above for the introduction of silent mutations into the DNA molecules of the invention.

Immunogenic Polypeptide and Conjugates

Because the full amino acid sequence of the p110 sEGFR/sErbB1 has been elucidated by the present invention, the invention also provides polypeptides useful for generating antibodies specific to the proteins encoded by the amino acid sequences of the invention, including SEQ ID NO: 1, SEQ ID NO: 3, SEQ ID NO: 4, SEQ ID NO: 5, and SEQ ID NO: 6. By utilizing a portion of the sEGFR/sErbB1 sequence which contains some of the 78 novel amino acids of the carboxy terminus of the disclosed sEGFR/sErbB1 proteins, antibodies raised to these peptides may be specific for the placental p110 sEGFR/sErbB1, but non-reactive with full length EGFR or other sEGFR/sErbB1 isoforms such as p60 sEGFR/sErbB1. Thus, polyclonal or monoclonal antibodies particularly useful for detecting p110 sEGFR/sErbB1 in patient samples may be made using the disclosed 78 amino acid sequence.

Polypeptides for use as immunogens will typically be smaller than the full sEGFR/sErbB1 protein, ranging from 10 to about 500 amino acids in length. Although they may contain other amino acids for, e.g., conjugation purposes, the immunogenic polypeptides of the invention comprise an amino acid sequence specific for sEGFR/sErbB1 which is of 10 to 25 amino acids in length, more preferably 11 to 21 amino acids in length, and most preferably 14 to 20 amino acids in length. These lengths of specific sequence are typical of those used in the art for conjugation to immunogenic carrier molecules. The amino acid sequence is identical to an amino acid sequence of similar length in an amino acid sequence selected from the group consisting of amino acids 628-705 of SEQ ID NO. 1, amino acids 628-705 of SEQ ID NO. 3, amino acids 628-705 of SEQ ID NO. 4, amino acids 628-705 of SEQ ID NO. 5, and amino acids 628-705 of SEQ ID NO. 6. The polypeptides may optionally comprise further portions of the sEGFR/sErbB1 amino acid sequence which are not specific for the p110 sEGFR/sErbB1s, e.g., a peptide encoded by exon 15, 15a, and/or 15b of sEGFR/sErbB1.

These polypeptides may be conveniently conjugated to immunostimulatory carrier molecules. Preferred carrier molecules for use in immunogenic conjugates include keyhole limpet hemocyanin (KLH), ovalbumin, and bovine serum albumin (BSA), however, other suitable carriers may be used. Conjugation chemistries for this purpose are well known in the art, and are available in prepackaged kits (e.g., from Sigma-Aldrich.) Once conjugated, the immunogenic peptide-carrier conjugates may then be used to immunize animals to produce monoclonal or polyclonal antibodies. Standard injection regimes, with our without the use of adjuvants (alum, Freunds's, etc.), may be used to produce the desired immune response.

After harvesting, monoclonal or polyclonal antibodies produced using the above polypeptides, which are specific for p110 EFGRs, and which do not cross-react with other ErbB1 isoforms, may be selected by screening for binding to recombinant p110 sEGFR/sErbB1 and p170 EGFR, as described in the Examples below.

Immunoassays for sEGFR/sErbB1s, and their Diagnostic Uses

An important aspect of the invention is a sandwich immunoassay method for detecting or determining the concentration of soluble human epidermal growth factor receptor in a biological sample obtained from a patient. The method comprises: a) contacting an amount of a first purified antibody that specifically reacts with a first epitope of the extracellular ligand binding domain of sEGFR/sErbB1 with the patient biological sample to be tested, wherein the first purified antibody is modified with a first labeling moiety, b) contacting the sample with an amount of a second purified antibody that specifically reacts with a second epitope of the extracellular ligand binding domain of sEGFR/sErbB1, wherein the second purified antibody is modified with a second labeling moiety, and wherein the second purified antibody does not competitively inhibit the binding of the first purified antibody, and c) determining the presence or amount of the soluble epidermal growth factor receptor complexed with said antibodies by detecting the co-presence of the first and second labels.

In preferred embodiments of the assays of the invention, one antibody is either MAb R.1 or an antibody which binds to the same epitope as MAb R.1. In preferred embodiments, the second antibody is MAb 528, or an antibody which binds to the same epitope as MAb 528. Antibodies may be tested for common epitopes by competitive binding assays according to methods standard in the immunochemical arts. Competitive binding assays using p170 ErbB1, p110 sEGFR/sErbB1, or any other ErbB1 isoform with ligand binding subdomains I-IV may be used as the antigen in a competitive binding assay to determine antibodies for use in the assays of the invention.

It is not intended that the above assays be limited to any particular immunochemistry format. Thus, standard sandwich, soluble sandwich, and competitive binding formats are envisioned for use in the assays of the invention. However, applicants have found that a standard sandwich assay format, such as described in Example V, works well, and thus will be used to generally describe the assay. In this format, the first labeling moiety is a binding moiety, such as a hapten or biotin. The first labeled antibody is then bound to a streptavidin or avidin coated solid support, such as a microliter plate well. This serves as a detection mechanism for the first labeling moiety, as the location of the moiety (i.e., bound to the well of the microliter plate) is then known. After the first antibody is bound to the wells, a patient biological sample may then be introduced into the wells.

In preferred embodiments of this aspect of the invention the patient biological sample is chosen form the group consisting of blood, serum, plasma, urine, saliva, sputum, breast nipple aspirates, and ascites fluid. Especially preferred samples are serum, and plasma. After incubation with the first antibody, the wells are rinsed, and then the second labeled antibody is added. In this format, the second labeling moiety is a detectable labeling moiety such as a fluorescent, colorigenic, or chemiluminescent moiety. A preferred moiety for use as the second labeling moiety is acridinium, as the applicants have found its strong signal useful in determining especially low concentrations (femtomolar range). After incubation with the second antibody, the wells are again rinsed. Proper reaction components are then added, and the second labeling moiety detected by fluorometry, colorimetry, or luminometry. Thus, the co-presence of the two labels is determined by their location (attached to the well) and their detectable product (fluorescence, light, or colorimetric product).

The invention further provides a diagnostic method for determining the presence, or risk, of an ovarian carcinoma in a female human patient. The method comprises a) determining the concentration of soluble EGFR/ErbB1 in a biological sample obtained from a female patient (e.g., by the above immunochemical method b) comparing the concentration obtained in a) with a normal or baseline level for soluble EGFR/ErbB1 established with samples from female humans without ovarian cancer, and c) correlating a decrease in the concentration of sEGFR/sErbB1 in the patient's sample with the presence of an ovarian carcinoma in the patient. A baseline for an assay of the invention may be established from biological samples from healthy patients, as in Example VI. It is desirable to establish baseline concentrations for a range of ages and physiological conditions (such as pre/post menopause) in order to better match the baseline value to the patient being tested. As shown in Example VII, the presence of ovarian cancer in female patients is strongly correlated with a reduced serum sEGFR/sErbB1 concentration in those patients. Thus, the assays of the invention may be useful for screening patients for ovarian cancer using simple phlebotomy samples.

In further embodiments of the assay of the invention, a female patient may be monitored with repeated testing to determine the onset or progression of ovarian cancer. Repeated testing may be done as a yearly screening of a patient to better detect the onset of disease, or at shorter intervals if a patient is at high risk for the disease. Additionally, the female patient may be tested before and after radiation, chemotherapy, or surgical treatment to monitor the regression or progression of ovarian cancer. This follow-up testing may be done at regular intervals, such as monthly or weekly, or at other intervals if indicated by the patient's condition. As shown in example VII, the serum levels of female patients with ovarian cancer may change over the course of treatment, indicating an improved prognosis. Conversely, a decrease in serum sEGFR/sErbB1 levels may be used to catch remission of the disease, or recurrences after cytoreductive surgery.

The results presented show that ovarian cancer patients with survival times twice that of the mean survival times of patients with ovarian cancer had detectable levels of sEGFR/sErbB1 while patients with average, or less than average, survival times had significantly reduced levels of sEGFR/sErbB1. Thus, the absence, or low levels, of sEGFR/sErbB1 may be indicative of aggressive disease.

The following examples are offered to further illustrate the various aspects of the present invention, and are not meant to limit the invention in any fashion. Based on these examples, and the preceding discussion of the embodiments and uses of the invention, several variations of the invention will become apparent to one of ordinary skill in the art. Such self-evident alterations are also considered to be within the scope of the present invention.

Example I

Isolation and Characterization of Human EGFR/ERBB1 cDNAs Encoding Soluble EGFRs

To isolate human EGFR clones that lack sequences encoding the cytoplasmic domain, but have the extracellular domain, differential hybridization was employed to screen an oligo-dT primed human placental cDNA library (Clontech, cat. # H1144x). The library was screened for clones that were positive for a ligand binding domain (LBD) specific probe (positions 174-2105), but negative for a kinase domain (KD) probe (see FIG. 2 for full length/p110 comparison).

The ligand binding domain probe was synthesized by the PCR using pXER as a template (Chen et al., Nature, 32, 820 (1987)). The forward primer was: SEQ ID NO: 7, corresponding to nucleotide positions 174-193. The reverse primer had the sequence SEQ ID NO:8, representing base pairs 2086-2105. Nucleotide numbering is according to Ullrich et al., supra, unless stated otherwise. Amplification was performed for 35 cycles (94° C. for 1 minute; 65° C. for 1 minute; 72° C. for 3 minutes) with a final extension at 72° C. for 10 minutes. The PCR product was then excised from a low melting point agarose gel. A 768 by EcoRI fragment from pXER was gel purified and used as the intracellular kinase domain (KID) probe. The LBD and KD probes were radiolabeled with [$\alpha$-$^{32}$P]dCTP using a random primer DNA labeling kit (Gibco BRL) according to the manufacturer's instructions. The hybridizations were performed in a solution containing 6×SSC, 5×Denhard's, 7.5% dextran sulfate, 0.5% N-lauryl sarcosine, and 100 μg/ml salmon sperm DNA at 65° C. Filters were washed in 0.1×SSC and 0.1% N-lauryl sarcosine at 65° C. and then were exposed to x-ray film for 24 to 72 hours at −80° C. with an intensifying screen.

Several clones hybridizing exclusively to the LBD probe were purified. Plasmid DNA, which contained inserts of interest, was released from the pλDR2 vector by site-specific recombination using the CRE-lox system (Murphy et al., supra). Inserts were sequenced on both strands using the Taq DyeDeoxy cycle sequencing kit and the Applied Biosystems model 373A automated DNA sequencer.

To determine whether the transcript encoding p110 sEGFR/sErbB1 is expressed in human placenta, RNA from a human placenta cell line (ATCC, CRL 1584) was isolated by a guanidine isothiocyanate procedure. Isolated RNA was treated with RNase free DNase and extracted twice with 1:1 phenol:chloroform. RNA (1 μg) was heated to 90° C. for 5 minutes, then the RNA was reverse transcribed in a 20 μl reaction containing 1× Avian Myeloblastosis Virus (AMV) reaction buffer, 1 mM each dNTP, 10 mM dithiothreitol (DTT), 20 U RNAsin, 10 U AMV reverse transcriptase, and 0.1 μg oligo-dT at 24° C. for 10 minutes, 42° C. for 50 minutes, 99° C. for 5 minutes and then 4° C. for 5 minutes. The first strand cDNAs were then amplified by adding Taq polymerase to the reverse transcription reaction along with pEX15 F (SEQ ID NO:9) and pEX15R (SEQ ID NO:13) in a final volume of 100 μl under the amplification conditions described hereinabove. The amplified products were analyzed by 5% PAGE. The results show that the 3.0 kb transcript is expressed in the human placenta cell line.

Thus, the isolated clone represents a 3.0 kb alternative transcript of EGFR. To map the 3.0 kb transcript, the following primers were employed: P1981 (EX15 F; SEQ ID NO:9), P267 F (EX15bF; SEQ ID NO:10), P615 F (EX15bF; SEQ ID NO:11), P297R (EX 15bR; SEQ ID NO:12) and P732R (EX15bR; SEQ ID NO:13). The 3.0 kb transcript arises from an alternative splicing event from exon 15 to a novel exon located within intron 15 of the EGFR gene. This novel exon contains 2 polyadenylation sites. None of the downstream EGFR exons are included in this transcript. This transcript differs from the 2.8 kb transcript unique to A431 cells as the A431 transcript contains EGFR exons 1 to 16 and then splices to an unrelated sequence derived from a translocation. The 3.0 kb transcript encodes a polypeptide of 681 amino acids (less the 24 amino acid signal peptide) (SEQ ID NO:1) containing 78 unique carboxy-terminal amino acids Pro 628-H is 705 of SEQ ID NO: 1.

Other variant unique EGFR-related sequences that have been detected by either cDNA cloning or by PCR include truncation at amino acid Phe 641 (SEQ ID NO:3), Gln to Arg at amino acid 657 (SEQ ID NO:4), Pro to Leu at amino acid 661 (SEQ ID NO:5), and Ser to Phe at amino acid 703 (SEQ ID NO:6).

Therefore, soluble isoforms of human EGFR, as well as amino acid variants of these sEGFR/sErbB1s, are expressed in placental tissue.

Example II

Soluble Human EGFR/ERBB1R1Gene Product

The amino acid sequence deduced from the 3.0 kb EGFR/ERBB1 cDNA, (SEQ ID NO:1), predicted a 705 amino acid polypeptide with a molecular mass of 77 kD. The first 24 amino acids code for a signal peptide; following cleavage by signal peptidases, the predicted molecular weight of this polypeptide is 75 kD. The sequence encodes subdomains I, II, III and a portion of subdomain IV of the extracellular ligand binding domain of the EGFR plus an additional 78 unique carboxy-terminal amino acids. A quail fibroblast cell line, QT6, was transiently transfected with the plasmid pDR2241, which contains the 3.0 kb EGFR/ERBB1 transcript and synthesizes a 110 kD glycosylated polypeptide (p110 sErbB1). Cells were transfected with 15 μg of pDR2241 by the calcium phosphate precipitation technique as described previously (Ausubel et al., Current Protocols in Molecular Biology, John Wiley & Sons, NY (1994)).

Transfected cells from two 10 cm plates were pooled and replated in 6 well plates approximately 48 hours post-transfection. The following day, cells were rinsed once in phosphate buffered saline (PBS) and labeled in methionine free DMEM supplemented with 5% dialyzed FCS and 150 μCi/ml of [$^{35}$S] methionine (Promix, Amersham) at 37° C. for 12 hours. Conditioned medium from labeled cells was collected and centrifuged briefly to remove loose cells and debris and phenylmethylsulfonyl fluoride (PMSF) and aprotinin were added to a final concentration of 1 mM and 50 μg/ml. Cell monolayers were lysed and immunoprecipitated with the addition of 1 to 5 μg of monoclonal antibody as described previously (Maihle et al., Mol. Cell. Biol., 8, 4868 (1988)). Samples were resuspended in 2× Laemmli sample buffer (125 mM Tris-HCl, pH 6.8, 4% SDS, 20% glycerol, 10% 2-mercaptoethanol, 2 mM EDTA, 0.04% bromphenol blue), boiled for 5 minutes and separated by 10% SDS-PAGE. Gels were stained with Coomassie blue, treated with EnHance (Dupont) and dried before an overnight exposure to x-ray film.

Immunoprecipitation of mock transfected cells failed to reveal a specific EGFR related polypeptide in either cell lysates or in conditioned media, while a 115 kD soluble EGFR was immunoprecipitated from the media of control A431 cells. Immunoprecipitation of cell lysates from transfected cells revealed a heterogeneous 110 kD species that was specifically recognized by the EGFR specific monoclonal antibody, R1 (Amersham, RPN 513) (Waterfield et al., J. Cell. Biochem., 20, 149 (1989)). Thus, expression of the nucleic acids of the invention encoding soluble isoforms of the human EGFR results in a glycosylated sEGFR/sErbB1 protein when transgenically expressed in eukaryotic cells.

Example III

Growth Inhibitory Potential of Soluble ErbB1Receptors on Ovarian Carcinoma Cell Growth in Vitro To examine the affect of p110 sErbB1 on EGFR-regulated cell growth, stable CHO cell lines expressing p110 and/or EGFR have been established and clonally isolated. Co-expression of p110 sErbB1 in cells expressing p170 EGFR results in the rapid and unexpected induction of cell rounding (24 hr) and programmed cell death (48 hr). See FIG. 5. We have verified that the mechanism of cell death is apoptotic based on nuclear morphology, and Hoechst staining. Interestingly, cell death does not occur in CHO cells treated similarly but expressing a truncated EGFR mutant that has lost most of its extracellular domain (i.e., the type III variant, originally cloned from a human glioma). These results were initially discovered using transient transfection analyses, but since that time inducible expression of p110 in CHO cells has been established using an ecdysone promoter system (Invitrogen), and have found identical results using this inducible system. These results suggest that p110 sErbB1 may be able to interfere with EGFR-dependent cell substrate attachments, and hence cell survival, and that these attachments are dependent on the extracellular domain of the EGFR.

To determine the function of the human 3.0 kb alternative transcript which encodes p110 sErbB1, a quantitative ribonuclease protection assay was used to determine its relative abundance in RNA from 17 adult (brain, breast, colon, heart, kidney, liver, lung, pancreas, placenta, prostate, skeletal muscle, small intestine, spleen, stomach, testis, thymus, and uterus) and 4 fetal tissues (brain, kidney, liver, and lung), as well as in numerous carcinoma-derived cell lines, either with or without EGFR gene amplification. The riboprobe consisted of 313 nt (1754-2066 in X00588) shared by both the full-length and the 3.0 kb transcripts, plus 134 by of exon 15B which was specific for the 3.0 kb mRNA. Transcripts containing exon 15B would result in a protected fragment of 447 nts, whereas those containing exon 15 spliced to exon 16 would result in a protected fragment of 313 nts. The full-length transcripts were observed in all of the samples examined, while the 3.0 kb transcript was detected only in human placenta, and in the carcinoma cell lines which also contained amplification of the EGFR gene. The relative ratio of full-length to 3.0 kb transcripts was quantified using a phospho-imager. The relative level of the full-length mRNA was ~200-fold greater than the level of the 3.0 kb transcript in both human placenta and in the MDA-MB-468 breast carcinoma cell line, which contains ~15-fold amplification of the EGFR gene (Filmus et al., 1985). However, in the A431 carcinoma cell line containing ~30-fold amplification of the EGFR gene, the full-length transcript was only present in 100-fold excess compared to the 3.0 kb mRNA. The 3.0 kb transcript was not detected in the absence of EGFR gene amplification in other carcinoma-derived cell lines.

Normal cells are expected to tolerate co-expression of p110 sErbB1 with EGFR because these proteins may route to distinct membranes (i.e., apical vs. basolateral), whereas co-localization of these receptors may result in apoptosis. Accordingly, the loss of cell polarity/membrane organization, which is characteristic of high-grade carcinomas, may result in selection against p110 sErbB1 expression in ovarian tumors.

Once the integrity of the soluble receptor, produced as described in Example II, has been established (i.e., by mobility as a discrete band of the appropriate molecular weight on an SDS gel) serial dilutions of these preparations are added to the culture media (MEM-α reduced FCS, +/−recombinant EGF/TGF-α (Collaborative Research)) of selected (c-erbB expressors vs. nonexpressors) ovarian carcinoma cells to assay their effect on cell growth. Changes in cell growth rates are determined by monitoring $^3$H-thymidine incorporation, and by using an MTT cell growth assay.

Example IV

Preparation of Monoclonal Antibodies

By utilizing polypeptide sequences derived from the unique 78 amino acid carboxy-terminus of SEQ ID NO: 1, 3, 4, 5, or 6, specific monoclonal antibodies may be produced to SEQ ID NO: 1, 3, 4, 5, or 6 (note: as the unique carboxy terminus of SEQ ID NO: 3 is a portion of SEQ ID NO: 1's carboxy terminus, antibodies raised using some or all of the first 14 amino acids of the 78 amino acid carboxy terminal sequence of SEQ ID NO: 1 may react with SEQ ID NO: 3). Applicants note that the total number of sequences which may be tested for antigenicity if 10 amino acid polypeptides are used, and sequences are generated by "walking' along the amino acid sequence, would be 91 (68 for SEQ ID NO: 1, 10 unique sequences for SEQ ID NO: 4, 10 unique sequences for SEQ ID NO: 5, and 3 unique sequences for SEQ ID NO: 6). This number is quite manageable, given modern polypeptide production techniques and facilities for mass testing of hybridoma candidates, and does not represent undue experimentation for one of ordinary skill in the art (predetermined peptide sequences may be ordered on the World Wide Web, and sent to available commercial services to generate hybridomas). Thus, monoclonal antibodies may be prepared by analogy to the methods described below for the preparation of subdomain I, III, and IV specific antibodies.

To prepare monoclonal antibodies (MAbs) specific for epitopes present in domains I, III or IV of full-length human EGFR, synthetic peptides were prepared. The peptides were predicted to have a high hydrophilicity, surface probability, and antigenicity. The peptides correspond to amino acids 77 to 93 of subdomain I (SEQ ID NO:14), 290-311 of subdomain III (SEQ ID NO:15), 352-369 of subdomain III (SEQ ID NO:16), and 556-567 of subdomain IV (SEQ ID NO:17) of the complete ErbB1 receptor, which lacks the signal peptide. Peptide immunogens were made by coupling the peptides to keyhole limpet hemocyanin and bovine serum albumin. The maleimide coupling chemistry required the addition of cysteines to the carboxy-terminus of the 77 to 93 and 352-369 peptides, while the native cysteines of the 290-311 and 556-567 peptides were used for coupling.

Although every immunized mouse elicited an immunological response toward its cognate peptide, as determined by ELISA, only mice injected with peptides having SEQ ID NO:15, SEQ ID NO:16 or SEQ ID NO:17 produced antibodies capable of recognizing the 170 kD ErbB1 receptor (p170) from A431 whole cell lysates by Western blot. Hybridomas from mice injected with peptides having amino acids 290 to 311 (clone 10B7), 352-369 (clones 15E11 and 17H3), and 556-567 (clone 2D2) of the mature EGFR were generated. All of these clones produced monoclonal antibodies that recognized p170 ErbB1 in Western blots, and that bound to A431 cells as detected by immunofluorescence microscopy. Two MAbs (15E11 and 2D2) were also compatible with immunohistochemical methods, whereby cells or tissues are embedded in paraffin, sectioned, treated with steam and citrate to retrieve masked antigens, immunolabeled, and processed to visualize antigen with diaminobenzidine.

Three MAbs (10B7; 15E11, and 2D2) were able to immunoprecipitate p170 ErbB1 from whole cell lysates of A431 cells. One of these MAbs (15E11) immunoprecipitated a 60 kD soluble form of human sErbB1 (p60) from whole cell lysates and culture media of transfected QT6 quail fibroblasts (QT6/pDR161). MAb 15E11 also detected p60 sErbB1 in QT6/pDR161 culture media by ALISA (acridinium-linked immunosorbent assay). MAb 15E11 was covalently coupled to Protein G and this resin was employed to purify (80% homogeneity) p60 ErbB1 from QT6/pDR161 culture media by immunoaffinity chromatography. This MAb reacted in the same manner to p110 ErbB1.

Hybridoma clones 10B7, 15E11, 17H3 and 2D2 have been deposited with the American Type Culture Collection, in accord with the requirements of the Budapest Treaty, and granted Accession Nos. HB-12204, HB-12205, HB-12206, and HB-12207, respectively.

Example V

ALISA for Detection of the sErbB1 Isoforms (sEGFR/sErbB1s) in Human Sera and Cell Culture A sensitive acridinium-linked immunosorbent assay (AL-ISA) to quantify sErbB1/sEGFR and EGFR/ErbB1 molecules in patient body fluids and tissues, respectively, was developed by applicants. This ALISA as described below was used to quantify serum sErbB1 levels in healthy men and women, as further described in Example VI, and in patients with ovarian cancer. The experimental results of Baron et al., J. Immunol. Methods, 219, 23 (1998) are incorporated by reference. The ALISA was developed using the following:

Antibody Reagents and Analytes

Sheep anti-ErbB1 antiserum (cat. #06-129) was obtained from Upstate Biotechnology (Lake Placid, N.Y.). Antiserum #06-129 was prepared against a recombinant fusion protein that embodies exons 15-18. Because exon 17 encodes the transmembrane domain, this protein embodies extracellular, transmembrane, and cytoplasmic amino acid sequences. Mouse MAbs specific for ErbB1 ECD were obtained from various commercial sources: MAb R.1 (Amersham Life Science, Arlington Heights, Ill.; Oncogene Research Products, Cambridge, Mass.; Santa Cruz Biotechnology, Santa Cruz, Calif.), MAb C11 (Cambridge Research Biochemicals, Valley Stream, N.Y.), MAb 528 (Oncogene Research Products; Santa Cruz Biotechnology), MAb 225 (Oncogene Research Products), MAb LA1 (Upstate Biotechnology), MAb LA22 (Upstate Biotechnology), MAb 111.6 (NeoMarkers, Freemont, Calif.), MAb 199.12 (NeoMarkers). MAbs 10B7, 15E11, 17H3, and 2D2 disclosed above are specific toward peptide epitopes of ErbB1 ECD. MAb 20H5 (Sanders and Salisbury, 1994), which is specific for the cytoskeletal protein centrin, was used as a control antibody.

Purified p170 ErbB1, which is used as our standard analyte, was purchased from Sigma (St. Louis, Mo.). The protein concentration of p170 ErbB1 given by Sigma was confirmed by quantitative amino acid analysis. Briefly, p170 ErbB1 was transferred to 6×50 mm borosilicate tubes, dried, placed in a larger vial with 200 µl of 6 N HCl plus 1% phenol for hydrolysis under vacuum for 24 hours. The hydrolyzed amino acids were injected onto a Beckman 6300 Amino Acid Analyzer using sodium buffers (Beckman Instruments, Fullerton, Calif.). Chromatographic data were collected and analyzed with Beckman System Gold software, using norleucine as an internal amino acid standard. The concentration of p170 ErbB1 was determined by total recovery of alanine, phenylalanine, and proline in comparison to norleucine. The control analyte, trpEcentrin, was purified and concentration determined by Bicinchoninic Acid Assay (BCA) (Pierce Chemical, Rockford, Ill.).

Generation of QT6/psErbB1ECD589

A cDNA fragment encoding 589 amino acids of the human EGF receptor's ECD was subcloned from pXER (Chen et al., 1989; a.k.a. pXEGFR, Opresko et al., 1995) into pcDNA3 (Invitrogen, Carlsbad, Calif.). pXER was digested with Nae I; an approximately 3.5 kb cDNA fragment was resolved by agarose gel electrophoresis and gel purified using GENECLEAN™ (BIO 101, La Jolla, Calif.). The 5'-Nae I restriction enzyme site was located within the pXER vector, whereas the 3'-Nae I site was positioned just before nucleotide 2026 of the EGFR/ERBB1/HER1 cDNA; the nucleotide numbering system is that of Ullrich et al. (1984). Xba I linkers (Boehringer Mannheim, Indianapolis, Ind.) were phosphorylated with T4 polynucleotide kinase and ligated to the blunt-ended approximately 3.5 kb Nae I restriction fragment with T4 DNA ligase. The linker-ligated restriction fragment was subsequently digested with Xba I to yield two DNA fragments of approximately 1.5 kb and approximately 2.0 kb. The larger approximately 2.0 kb EGFR/ERBB1/HER1 cDNA fragment encoding the ECD of ErbB1 was purified as described above and ligated to Xba I digested, calf intestine phosphatase treated pcDNA3. E. coli DH5-α were transformed with pcDNA3 constructs containing the approximately 2.0 kb EGFR/ERBB1/HER1 cDNA according to the method of Hanahan (Maniatis et al., 1982) and grown on Luria-Bertani agar plates containing 100 µg/ml ampicillin as a selectable marker. Plasmid DNA was isolated by the boiling method from transformed bacterial colonies (Ausubel et al., 1989) and digested with BamH I to determine the orientation of the approximately 2 kb EGFR/ERBB1/HER1 insert in pcDNA3. Plasmids containing the approximately 2 kb EGFR/ERBB1 fragment in the sense orientation yield a BamH I restriction fragment of 1348 bp, whereas clones containing the approximately 2 kb EGFR/ERBB1/HER1 fragment in the antisense orientation yield a 678 by restriction fragment. A transformed clone of E. coli DH5-α containing the approximately 2.0 kb EGFR/ERBB1/HER1 fragment in the sense orientation was identified and plasmid DNA, called psErbB1ECD589, was prepared using the QIAGEN plasmid purification kit (QIAGEN, Chatsworth, Calif.) for transfection experiments. The quail fibroblast cell line, QT6, was subsequently transfected with psErbB1ECD589 by calcium phosphate precipitation (Wigler et al., 1979) and stable, geneticin (G418) resistant cells were isolated and cloned by limiting dilution. A clonal cell line, QT6/psErbB1ECD589, expressing p100 sErbB1 was identified by immunoprecipitation of $^{35}$S-labeled cell lysates with MAb C11 using methods described previously (Maihle et al., 1988).

Cell Culture

All tissue culture cells were grown in $NaHCO_3$, buffered media at 37° C. in 5% $CO_2$ and air. All tissue culture reagents were purchased from Gibco BRL Life Technologies (Grand Island, N.Y.). A431, MDA-MB-453, and SK-BR-3 cells (ATCC) were maintained in Dulbecco's Modified Eagle Medium (DMEM) supplemented with 20 mM Hepes, pH 7.3, 10% fetal bovine serum (FBS), 1 mM sodium pyruvate, and 2 mM L-glutamine. QT6 quail fibroblasts (Moscovici et al., 1977; ATCC) and QT6 cells transfected with the plasmid vectors pDR161 or psErbB1ECD589, i.e., QT6/pDR161 (Reiter and Maihle, 1996) or QT6/psErbB1ECD589, respectively, were grown in DMEM supplemented with 20 mM Hepes, pH 7.3, 4% heat inactivated FBS, 1% chicken serum, 1 mM sodium pyruvate, and 2 mM L-glutamine.

Generation of Whole Cell Lysates for ALISA

Tissue culture cells at 80% to 90% confluence were rinsed once with phosphate buffered saline (PBS; 10 mM $KH_2PO_4$/$K_2HPO_4$, 150 mM NaCl, pH 7.2), scraped from the PBS loaded petri dish with a cell lifter (Costar, Cambridge, Mass.), and harvested by centrifugation at approximately 1000×g for 5 minutes. The cell pellet was resuspended and lysed by adding a 1:10 (w/v) ratio of membrane protein immunoprecipitation lysis buffer containing protease inhibitors (10 mM Trizma®, pH 7.4, 150 mM NaCl, 1 mM EDTA, 1% Nonidet P-40, 150 µg/ml phenylmethyl sulfonyl fluoride, 2 µg/ml aprotinin, 0.5 µg/ml leupeptin, 1 µg/ml pepstatin A). The cell lysate was vigorously vortexed for 30 seconds and sonicated (three 10 second bursts at half power with 60 second cooling periods) with a sonicator (model W-225R; Heat Systems-Ultrasonics, Farmingdale, N.Y.) to break DNA molecules. Enough 5.0 M NaCl was added to the cell lysate to bring the final NaCl concentration to 500 mM. Cellular debris was pelleted by centrifugation at 10,000×g for 10 minutes. The resulting supernatant was exchanged into Trizma buffered saline (TBS; 10 mM Trizma, pH 7.4, 150 mM NaCl) containing 0.02% $NaN_3$ by passage through a Sephadex G-25 fast desalting gel filtration column using a Fast Performance Liquid Chromatography system (FPLC; Pharmacia Biotech, Piscataway, N.J.), and concentrated by ultrafiltration with a Centricon centrifugal concentrator (Amicon, Beverly, Mass.). The protein concentration of the final whole cell lysate was determined by BCA (Pierce Chemical).

Acridinium Labeling Procedure

A 1 mg/ml stock solution of succinimidyl-activated acridinium ester [4-(2-succinimidyl-xycarbonylethyl)phenyl-10-acridinium-9-carboxylate sulfonate; ASSAY Designs, Ann Arbor, Mich.) in dry dimethyl formamide was stored in 5 µg aliquots at –70° C. MAb IgG was exchanged from carrier solution into labeling buffer (0.2 M sodium phosphate buffer ($NaH_2PO_4$/$Na_2HPO_4$) pH 8.0) with a Sephadex G-25 fast desalting gel filtration column by FPLC and concentrated by ultrafiltration to 200 µl and approximately 1.0 mg/ml total protein. MAb IgG was labeled at room temperature with a 1:80 molar ratio of IgG to succinimidyl-activated acridinium ester for 15 minutes in the dark. The coupling reaction was stopped by adding 100 µl of quenching buffer (labeling buffer with 10 mg/ml lysine monohydrochloride) and incubating for an additional 5 minutes. Unbound acridinium ester was removed with a Sephadex® G-25 fast desalting gel filtration column by FPLC and simultaneously exchanged into a solution containing 0.2 M sodium phosphate buffer, pH 7.3, and 0.02% NaN$_3$. Following buffer exchange by FPLC, the acridinium-labeled MAb IgG was concentrated by ultrafiltration to a volume of 100 μl; 1.0 ml of storage buffer (0.2 M sodium phosphate buffer, pH 7.3, 0.1% bovine serum albumin, 0.02% NaN$_3$) was added and the volume was reduced again to 100 μl. The Relative Light Units (RLU)/μl were determined and the final acridinium-labeled MAb IgG was stored at −70° C.

ErbB1 ECD-Specific Acridinium-Linked Immunosorbent Assay

White XENOBIND® 96 well microtiter plates (Xenopore, Saddle Brook, N.J.) were coated overnight at 4° C. with 25 μg/well of an affinity-purified goat anti-mouse IgG2b specific polyclonal antibody in carbonate buffer (90 mM NaHCO$_3$ 10 mM Na$_2$CO$_3$, pH 9.4, 0.02% NaN$_3$); the antigen is attached covalently to the plate under these conditions. All incubations were performed on a rocker platform. The plates were washed three times with high salt Tween-20® wash buffer (HST-20WB; 0.05% polyoxyethylene sorbitan monolaurate (Tween-20®, 20 mM Trizma®, pH 7.4, 500 mM NaCl, 0.02% NaN$_3$) blocked with ALISA blocking buffer (ALBB; 2.0% bovine serum albumin (BSA), 10 mM Trizma pH 7.4, 150 mM NaCl, 0.02% NaN$_3$) for 1 hour at room temperature, washed with HST-20WB, incubated with 0.05 μg/well anti-ErbB1 ECD-specific MAb R.1 diluted in ALBB for 2 hours at 37° C., washed three times with HST-20WB, incubated with analyte or unknown sample for 2 h at 37° C., washed three times with HST-20WB, incubated with acridinium-labeled anti-ErbB1ECD-specific MAb 528 (500,000 counts/well) for 1 hour at 37° C., washed three times with HST-20WB, and read with a luminometer (model LB 96P; EG&G Berthold Analytical Instruments, Nashua, N.H.). In order to maintain an even temperature across the microtiter plate, all 37° C. incubations were performed in a forced-air environmental shaker (model 3528; Lab-Line Instruments, Melrose Park, Ill.) that was modified to hold microtiter plates. Acridinium decomposition was initiated by sequentially adding a solution containing 0.441% nitric acid and 0.495% H$_2$O$_2$ followed by a solution containing 0.25 M NaOH and 0.1875% cetyltrimethylammonium chloride. This treatment drives the acridinium ester to form an unstable dioxetanone intermediate, which decomposes to form N-methylacridone in its excited singlet state; relaxation to the ground state results in the emission of photons of light at a wavelength of 430 nm (Weeks et al., 1986).

Positive and negative control analytes were p170 ErbB1 (Sigma) and a 60 kD trpEcentrin recombinant fusion protein (Baron et al., 1992), respectively. Analytes were prepared as dilution series in ALBB. Unknown samples included whole cell lysates, conditioned culture media, and human serum samples. All human sera were assayed at a 1:10 dilution in ALBB. Serial dilutions of whole cell lysates and conditioned culture media were made in ALBB. All assays were partially automated with a BIOMEK 1000 laboratory work station (Beckman Instruments, Palo Alto, Calif.).

ALSIA Results

As shown in FIG. 7, the above ALISA is specific for molecules containing subdomain IV of the extracellular domain of ErbB1 (p170 ErbB1, A431 mutant p110 sErbB1, recombinant p100 sErbB1), but does not bind to molecules which do not contain subdomain IV (p60 sErbB1 and other unrelated molecules). Also, as demonstrated in this and the following examples, the ALISA is highly sensitive, and can detect sErbB1 in the femtomolar range.

Immunoprecipitation and Characterization of sErbB1 Analogs from Normal Human Sera Blood from healthy men and women was collected by Mayo Medical Laboratories (MML), Department of Laboratory Medicine and Pathology, in accordance with an Institutional Review Board approved Normal Values Study Program. Each healthy donor was required to provide a recent physical history that included a physical exam and the results of the following tests: Hematology Group, Chemistry Group, Lipids, Thyroid Function, and Urinalysis. Chest x-ray and electrocardiogram also were performed on age appropriate subjects. Detailed clinical records from these healthy subjects are available. Blood was allowed to clot at room temperature for 30 min. The serum was separated from the clot and cells by centrifugation at 2000×g for 10 minutes, divided into 1 ml aliquots, and stored at −70° C. All serum samples from MML were collected between 1981 and 1984. Each serum sample was thawed after transfer to our laboratory, aliquoted into smaller volumes, and refrozen at −70° C. to prevent sErbB1 degradation. Each serum sample was, therefore, frozen and thawed only twice before measurement by ALISA.

Normal human sera were cleared of lipids with Seroclear® according to the manufacturer's protocol (Calbiochem-Novabiochem, La Jolla, Calif.), diluted 1:5 (v/v) in Affi-Gel Protein-A MAPs II® binding buffer (Bio-Rad Laboratories, Hercules, Calif.) and clarified of human IgG molecules by passage through a Protein-G Superose® affinity column by FPLC using Affi-Gel Protein-A MAPs II® binding, elution, and regeneration buffers (Bio-Rad Laboratories). The column flow through was collected, concentrated by ultrafiltration, exchanged into TBS containing 0.02% NaN$_3$ by FPLC with a Sephadex® G-25 fast desalting gel filtration column, divided into four aliquots, and immediately incubated with uncoupled (MAb minus) or MAb R.1-, 225-, and 528-coupled affinity resins. Alternatively, human serum samples were simply clarified of human IgG molecules by incubating with Immunopure® Immobilized Protein-G resin (Pierce Chemical) for 30 minutes at room temperature prior to immunoprecipitation. Both methods yielded identical immunoprecipitation results. The MAb R.1, 225, and 528 affinity resins were prepared with an Immunopure® Immobilized Protein-G IgG Orientation kit according to the manufacturer's instructions (Pierce Chemical); the MAb minus resin was prepared in an identical manner, except that no IgG was bound to Protein-G. Bound proteins were eluted from these resins with MAPs II® elution buffer, adjusted to neutral pH by adding 1.0 M Trizma® buffer (pH 9.0), and analyzed by SDS-PAGE and Western immunoblot. SDS-PAGE was performed in 1.0 mm thick vertical slab minigels (7×8 cm) with a Mini-PROTEAN II apparatus (Bio-Rad Laboratories). The stacking gel contained 3% acrylamide and the resolving gel contained 10% acrylamide (Laemmli, 1970). All SDS-PAGE samples were prepared with 4× Laemmli sample buffer (250 mM Trizma®, pH 6.8, 8% SDS, 40% glycerol, 20% 13-mercaptoethanol, 4 mM ethylenediaminetetraacetic acid, 0.08% bromphenol Blue) and boiled for 1 minute prior to electrophoresis. Gels were processed for Western immunoblot analyses.

Following SDS-PAGE, proteins were transferred to Immobilon® polyvinylidene difluoride (PVDF) membrane (Millipore, Bedford, Mass.) using a Type 1, Milliblot™ Graphite Electroblotter System (Millipore) according to the manufacturer's protocol. The membrane was allowed to air dry completely following protein transfer. The dry membrane was wet again with methanol, washed three times with Tween-20® wash buffer (T-20WB; 10 mM Trizma pH 7.4, 0.05% Tween-20®, 150 mM NaCl), and blocked with Nonfat Dry Milk (NFDM; 5% nonfat dry milk, 10 mM Trizma, pH 7.4, 150 mM NaCl, 0.02% NaN$_3$) at 4° C. overnight. NFDM blocking was followed by a second blocking step with 0.5% Boehringer Blocking Reagent (Boehringer Mannheim) in TBS with 0.02% NaN$_3$ at 37° C. for 1 hour. The membrane was rinsed briefly with T-20WB, incubated with primary antibody reagent (mixture of MAbs 15E11, 2D2, LA22, and C11 or MAbs 10B7, 15E11, 17H3, 2D2, LA22, C11, 111.6, and 199.12 alone) at 37° C. for 1 hour, washed with T-20WB for 1 hour, and incubated at 37° C. for 1 hour with peroxidase-conjugated goat anti-mouse antibody. Primary antibody reagents consisted either of neat conditioned culture media for MAbs 10B7, 15E11, 17H3, and 2D2 or of purified IgGs for MAbs LA22, C11, 111.6, and 199.12; each purified MAb was used at a final concentration of approximately 1 µg/ml. Conditioned culture media containing MAb consisted of RPMI-1640 medium supplemented with 10% or 20% FBS, 20 mM Hepes, pH 7.3, 2 mM L-glutamine, 1 mM sodium pyruvate, and 0.01% thimerosal (mercury [(o-carboxyphenyl)thio]-ethyl sodium) as a preservative. In some experiments, the membrane was washed with T-20WB and clamped into a multichannel Miniblotter™ (Immunetics, Cambridge, Mass.). Different channels were incubated with different primary antibody reagents at 37° C. for 1 hour, washed with T-20WB for 1 hour, and incubated at 37° C. for 1 hour with peroxidase-conjugated secondary antibody. To visualize antibody binding, the membrane was washed with T-20WB for 1 hour and reacted with the enhanced chemiluminescent substrate luminol (Amersham Life Science).

As shown in FIG. 14, a 110 kD protein was immunoprecipitated from normal human male and female sera with the ECD-specific anti ErbB1 antibodies used in the above ALISAMicrosequence analysis of partially pure p110 sErbB1 from human serum using Matrix Assisted Laser Desorpiton/Ionization-Time of Flight Mass Spectrometry shows that this protein is derived from the 3.0 kb alternative transcript having SEQ ID NO. 2 of the invention.

Comparison to Commercially Available ErbB1 ECD-Specific Enzyme-Linked Immunosorbent Assay (ELISA)

The EGFR ELISA (catalog #QIA35 from Oncogene Research Products) was performed exactly according to the manufacturer's instructions; i.e., standards and serum samples were diluted either into standard or sample diluent, respectively. This ELISA uses two MAbs that are specific for epitopes of the ErbB1 receptor ECD in a sandwich configuration; the origin and characterization of these MAbs has not been disclosed by the manufacturer. The second MAb used in the ELISA is biotinylated and binds peroxidase-conjugated streptavidin. Detection of ErbB1 is achieved by conversion of the chromogenic substrate tetra-methylbenzidine to a blue product by peroxidase, which is subsequently converted to a yellow product by the addition of stop solution (2.5 N sulfuric acid). The absorbance of the yellow reaction product was quantified with the spectraphotometry tool of a BIOMEK 1000 laboratory work station at 415 nm; a 560 nm reference filter was used for background subtraction.

Results of these experiments are shown in FIG. 15. Although the Oncogene ELISA did react with some substance in the sera of healthy men and women, it did not detect any difference in sErbB1 concentration between the two, nor did the ELISA results correlate with the applicants' ALISA results. Thus, the commercially available ELISA test differs substantially from the ALISA described herein.

Example VI

Establishment of Baseline sErbB1 Concentrations in Normal Male and Female Subjects In order to increase the usefulness of the above ALISA for determining abnormal sErbB1 values in patient sera, baseline or normal serum sEGFR/sErbB1 concentration values for men and women over a broad age range were established using the following methods:

Serum Samples

Blood from 88 healthy men and 144 healthy women was collected in accordance with a Mayo Foundation institutional review board-approved "Normal Values Study." Briefly, all blood samples were processed into serum and stored at ±70° C. until they were used. Serum sErbB1 levels were quantified for all the available samples. The gonadotropic and steroid hormone levels were measured in 83 of the 88 healthy men, and 123 of the 144 healthy women.

Menopausal Status Determination

Medical records were reviewed systematically to ascertain menopausal status at the time of the blood draw. Data collected include: date and patient age at the time of blood draw, date of last menstrual period (LMP), self-reported symptoms of menopause, date of surgical menopause (hysterectomy and/or oophorectomy), and FSH and/or LH levels. For patients who underwent surgical hysterectomy but not oophorectomy, the clinical records also were reviewed to determine the approximate date of clinical menopause (patient's self-report). The criteria used to assign menopausal status were one or more of the following: 1) age $\geq$ 60 years, 2) last reported menstrual period>six months from the date of the blood draw, 3) symptoms of menopause, 4) hysterectomy, 5) oophorectomy, 6) FSH level<30 IU/L (premenopause), or >36 IU/L (postmenopause). Menopausal status for 6 of the 144 women could not be determined in this study, because a) FSH levels were equivocal or there was insufficient serum to measure these levels, and b) the patient's medical record was incomplete; i.e., a long time interval between the patient's last medical visit and the blood draw or the patient transferred health care to another facility.

p110 sErbB1 ALISA

Serum p110 sErbB1 levels were determined by ALISA as outlined above in Example V. This ALISA specifically detects p110 sErbB1, and does not cross-react with p60 sErbB1, p105 sErbB2, or full-length ErbB2, ErbB3, or ErbB4. Initially, all sera were diluted 1:10 in ALISA blocking buffer (ALBB) and assayed in duplicate in three separate trials. Serum samples yielding relative light units (RLU's) below the linear range of the assay's standard curve were re-assayed either undiluted or diluted 1:5 in ALBB, whereas serum samples yielding RLU's above the linear range of the assay's standard curve were re-assayed either diluted 1:20 or 1:50 in ALBB. For each trial, the mean RLU's for each duplicate was determined and a corresponding sErbB1 concentration in fmol/ml was calculated. The final p110 sErbB1 concentration reported here, for each serum sample, is the median value from all three trials. The inter-assay biological detection limit for the p110 sErbB1 ALISAs performed was 10 fmol/ml.

Serum sErbB1 Levels Differ when Adjusting for Gender, Age, and Menopausal Status When unadjusted for age, serum p110 sErbB1 levels do not differ significantly between healthy men and women ranging in age from 20 to 79 years (See FIG. 8). We report a median serum p110 sErbB1 level of 6,816 fmol/ml (range: 837-42,533 fmol/ml) and 7,177 fmol/ml (range: 114-31,465 fmol/ml) for the men and women in this report, respectively. However, when taking age into consideration, we observe significant negative and positive associations between serum p110 sErbB1 levels and age in these healthy men (Spearman rank correlation coefficient=0.4562, p=0.0001) and women (Spearman rank correlation coefficient=−0.3491, p=0.0001), respectively (See FIGS. 9 A & B). Further analysis of sErbB1 levels with regard to menopausal status show that premenopausal and postmenopausal women have median serum p110 sErbB1 levels of 8,561 fmol/ml (range: 341-24,294 fmol/ml) and 3,400 finaI/ml (range: 114-31,465 fmol/ml), respectively (See FIG. 10). These data show that p110 sErbB1 levels are significantly higher in premenopausal women than postmenopausal women ($p<0.0001$). To determine if this difference is simply related to age, we next attempted to age match (±1 year) men to these groups of premenopausal and postmenopausal women. Although we were able to age match younger men to a subgroup of 71 premenopausal women, we were unable to age match enough older men to the postmenopausal group of women. We report a median serum p110 sErbB1 level of 8,740 fmol/ml (range: 747-24,294 fmol/ml) for the subgroup of premenopausal women and 5,883 fmol/ml (range: 837-28,602 fmol/ml) for the age-matched men (See FIG. 11). Interestingly, the serum p110 sErbB1 levels of the premenopausal women is also significantly higher than that of the younger men ($p=0.009$). These observations indicate that gender differences in serum sErbB1 levels exist between younger men and women, as well as between men and women 40 years and older. Moreover, these data suggest that the observed differences in sErbB1 levels between premenopausal and postmenopausal women are not simply a function of age, but may be modulated by the milieu of circulating gonadotropic and sex steroid hormones.

Example VII

Ovarian Cancer Patients Exhibit Significantly Reduced Serum sErbB1 Concentrations To explore the diagnostic potential of sErbB1, applicants utilized the ALISA described in Example V to compare pre-operative serum sErbB1 levels between 149 healthy women, 164 stage I, II, III, or IV ovarian cancer patients, 142 patients with benign ovarian tumors, and 115 patients with other benign gynecologic diseases of the pelvis. The individuals in each of these cohorts are within the same age range, but are not age-matched on a one-to-one basis. The cohort of patients with benign ovarian tumors had the following diagnoses: simple cyst, corpus luteum cyst, follicular cyst, dermoid, fibroma, mucinous cystadenoma, and serous cystadenoma; and the cohort of patients with other benign gynecologic pelvic diseases had the following diagnoses: paratubal cyst, cervical dysplasia, endometriosis, fibroids, and hydrosalpinx. The scattergram in FIG. 12 clearly shows that serum sErbB1 levels in EOC patients are significantly lower than those seen in healthy women (non-surgical patients), in patients with benign ovarian tumors, and in patients with other benign gynecologic pelvic diseases. Moreover, these data indicate that pre-operative serum sErbB1 levels may be useful in making a diagnosis between early, as well as late stage EOC versus benign ovarian tumor and other benign gynecologic pelvic disease.

Example VIII

Post-Operative Serum sErbB1 Concentrations of Ovarian Cancer Patients are Altered as Compared to Pre-Operative Concentrations The serum sErbB1 levels of ovarian cancer patients was tracked using the ALISA described in Example V according to the following methods:

Sample Collection and ALISA Methods

Blood from healthy women was collected by the Department of Laboratory Medicine & Pathology, Mayo Medical Laboratories, in accordance with an ongoing institutional review board-approved Normal Values Study program and processed into serum. All serum samples from healthy women used in this study were collected between 1981 and 1984.

Between 1985 and 1994, serum samples from women presenting to the Mayo Clinic for gynecological surgery were collected and stored to study the reproducibility of CA-125 measurements in women with EOC (60-63). Patients with ovarian cancer were classified as having International Federation of Gynecology and Obstetrics stage I, II, III, or IV disease at the time of staging laparotomy and tumor reductive surgery. Serum samples were considered preoperative if they were collected within 30 days prior to surgery. Patients with a prior diagnosis of EOC that had received previous cytoreductive surgery, radiation, or chemotherapy were eliminated from our study. We identified serum samples from 21 patients, ranging in age from 15 to 83 years, that fit these criteria.

Postoperative serum samples from patients with stage III or IV EOC were collected in accordance with North Central Cancer Treatment Group and Mayo Clinic Protocol 90-61-54, entitled "Cyclophosphamide plus carboplatin: comparison of conventional dose and double-dose carboplatin in patients with stage III or IV ovarian carcinoma—a Phase III study." All serum samples were collected between 1992 and 1994. Seventy-nine eligible patients were randomized to treatment on this study within 1 month after staging laparotomy and cytoreductive surgery.

Following collection, all blood samples were allowed to clot at room temperature for 30 min. The serum was separated from the clot and cells by centrifugation at 2000~X g for 10 min., divided into 1-ml aliquots, and stored at $-70°$ C. Each serum sample was thawed after transfer into our laboratory, aliquoted into smaller volumes, and refrozen at $-70°$ C. to prevent sErbB1 and EGF degradation. Each serum sample was, therefore, frozen and thawed only twice.

Serum sErbB1 levels were determined with an ALISA specific for epitopes of the ECD of ErbB1 according to Example V with the following ALISA blocking buffer (1.0% BSA, 10 mM Trizma, pH 7.4, 150 mm NaCl, 0.01% normal rabbit serum, 0.01% normal mouse serum, 0.02% $NaN_3$). Human sera were assayed undiluted or at dilutions of either 1:25 or 1:10 in ALISA blocking buffer. Initially, each serum sample was tested in duplicate at a 1:25 dilution in three separate experiments. Each serum sample was then tested in duplicate at a 1:10 dilution in three separate experiments. Finally, those serum samples that yielded undetectable sErbB1 levels at dilutions of 1:25 and 1:10 were tested undiluted in duplicate in three separate experiments. Undiluted serum samples that yielded values in relative light units below the interassay biological detection limit of 24 fmol/ml for this ALISA were considered undetectable. The sErbB1 concentration reported in the scattergrams for each serum sample represents the median of the mean sErbB1 level determined in three separate assays.

Results in Pre-Operative vs. Post-Operative Samples

Serum samples collected within a period of 30 days prior to staging laparotomy and cytoreductive surgery from 21 stage III or IV EOC patients were identified; none of these patients had received prior chemotherapy, radiation, or debulking surgery. We compared the serum sErbB1 levels in these EOC patients with the serum sErbB1 levels in a group of 21 healthy women of similar ages. The median (range) serum sErbB1 concentration of the 21 age-matched healthy women is 6,395 fmol/ml (1,846-23,708 fmol/ml). In contrast, the median (range) preoperative serum sErbB1 concentration of the 21 patients with stage III or IV EOC is 284 fmol/ml (30-1,350 fmol/ml). These data indicate that preoperative serum sErbB1 levels in patients with stage III or IV EOC are significantly lower than serum sErbB1 levels in healthy women of similar ages (Wilcoxon rank sum test, P<0.0001).

Serum samples collected after staging laparotomy and cytoreductive surgery were also examined from 73 patients with stage III or IV EOC who presented for treatment between 1992 and 1994. These patients had not received prior debulking surgery, radiation, or chemotherapy for EOC, and were enrolled in a phase III randomized clinical trial to study the efficacy of cyclophosphamide plus conventional dose carboplatin versus cyclophosphamide plus an intensive dose of carboplatin in patients with stage III and IV EOC following surgery.

The initial postoperative (0-34 days) serum sErbB1 levels in these 73 EOC patients were compared to serum sErbB1 levels in a group of 73 healthy age-matched women (FIG. 13). The median (range) serum sErbB1 concentration of the 73 healthy women was 6,113 fmol/ml (1,292-51,358 fmol/ml). In contrast, the median (range) initial postoperative serum sErbB1 concentration of the 73 EOC patients was 1,799 fmol/ml (nondetectable to 11,035 fmol/ml). These data indicate that the initial postoperative sErbB1 levels in patients with stage III or IV EOC differ significantly from sErbB1 levels in an age-matched group of healthy women Thirty-three patients enrolled in the aforementioned phase III study provided a second serum sample 35-287 days after cytoreductive surgery. The median (range) serum sErbB1 concentration of these 33 serum samples was 6,434 fmol/ml (non-detectable to 29,666 fmol/ml). The median (range) serum sErbB1 concentration of these 33 serum samples appeared similar to that seen in healthy women, with the exception of one patient who had an undetectable level of serum sErbB1 (See FIG. 13). It is noteworthy that the median serum sErbB1 concentrations for both the initial and second postoperative serum samples appear higher than those seen in preoperative serum samples of patients with stage III or IV EOC. Statistical comparisons of the sErbB levels in the serum samples collected 0-34 days after cytoreductive surgery with those in the serum samples collected 35-287 days after cytoreductive surgery in a group of healthy women were not performed, because these 33 serum samples represent a subset of the 73 patients enrolled in the phase III study and they were collected over a protracted time period, i.e., 253 days. Examination of the sErbB1 concentration in the initial versus the second serum sample for each of the 33 patients who underwent cytoreductive surgery shows that sErbB1 levels increased temporally for many, but not for all of these 33 patients during the course of combination chemotherapy. The sErbB1 level of one patient in fact decreased below detectable levels.

These results indicate the ALISA of Example V may be an important tool for monitoring the progression or regression of ovarian cancer in patients who are undergoing surgical, radiation, or chemotherapy treatments. The ability to monitor patient progress using sErbB1 as a marker may be especially useful in detecting post-surgical recurrence of the disease.

Example IX

Research Suggests that p110 sErbB1 is a gycosylphosphatidylinositol-Anchored Protein Research suggests that p110 sErbB1 is localized to the membrane via the addition of a glycosylphosphatidylinositol (GPI) anchor. The core structure common to all GPI anchors consists of a glycan bridge between phosphatidylinositol and phosphoethanolamine with phosphoethanolamine attached to the carboxy-terminus of the protein. GPI anchors are added to proteins containing an appropriate carboxy-terminal signal sequence. This linkage is a post-translational modification that occurs in the lumen of the endoplasmic reticulum within minutes of protein synthesis. The carboxy-terminal signal sequence consists of a cleavage/attachment site, called the omega site (ω), a short hinge region that contains charged amino acids, and a carboxy-terminal hydrophobic region of varying length. The carboxy-terminal signal sequences of several known GPI proteins, as well as the predicted signal sequences present in human p110 sErbB1 (and in an analogous mouse p110 sErbB1) are listed in Table 2. Compared to known GPI signal sequences, both the human (SEQ ID NO:18; SEQ ID NO:19) and the murine (SEQ ID NO:20) sErbB1 receptors contain potential carboxy-terminal GPI anchor signal sequences. In fact, the human p110 sErbB1 product contains 2 putative signal sequences; the significance of tandem signal sequences is not known, but potentially either could be used.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims.

We claim:

1. An assay for determining the concentration of a soluble epidermal growth factor receptor in a biological sample from a female patient, the assay comprising:
   a) obtaining a biological sample from the female;
   b) contacting an amount of a first purified antibody that specifically reacts with a first epitope of the extracellular ligand binding domain of soluble epidermal growth factor receptor with the biological sample to be tested, wherein the first purified antibody is modified with a first labeling moiety;
   c) contacting the sample with an amount of a second purified antibody that specifically reacts with a second epitope of the extracellular ligand binding domain of soluble epidermal growth factor receptor, wherein the second purified antibody is modified with a second labeling moiety, and wherein the second purified antibody does not competitively inhibit the binding of the first purified antibody;
   d) detecting the co-presence of the first and second labels to determine the concentration of the soluble epidermal growth factor receptor complexed with the antibodies; wherein one of the antibodies is chosen from the group consisting of mAb R.1 and an antibody which binds to the same epitope as mAb R.1; and wherein the other antibody is chosen from the group consisting of mAb 528 and an antibody which binds to the same epitope as mAb 528;
   e) comparing the concentration of soluble epidermal growth factor receptor obtained in step d) with a normal value; and
   f) correlating a decrease in the concentration of soluble epidermal growth factor receptor in the patient biological sample with the presence of an ovarian carcinoma in the patient.

2. The assay of claim 1 wherein the normal value is obtained by assaying biological samples from females of approximately the same age as the patient.

3. The assay of claim 1 further comprising the step of performing a second assay on a biological sample obtained from the patient at a point in time after the initial assay.

4. The assay of claim 3, wherein the patient has undergone treatment for ovarian cancer selected from the group consisting of chemotherapy, radiation therapy, and surgical treatment in the interval between the initial and second assay.

5. The assay of claim 3, further comprising the step of correlating an increase in the concentration of soluble epidermal growth factor receptor in the patient biological sample with an improved prognosis in the ovarian cancer condition.

6. The assay of claim 3, further comprising the step of correlating a decrease in the concentration of soluble epidermal growth factor receptor in the patient biological sample with a declining prognosis in the ovarian cancer condition.

7. The assay of claim 1 wherein the patient biological sample is chosen from the group consisting of urine, and ascites.

8. The assay of claim 1 wherein the patient biological sample is chosen from the group consisting of blood, serum and plasma.

9. The assay of claim 1 wherein the first labeling moiety is an affinity binding moiety.

10. The assay of claim 9 wherein the affinity binding moiety is biotin.

11. The assay of claim 10 wherein detection of the presence of the first labeling moiety is by binding of the biotin moiety to a solid support coated with a molecule chosen from the group consisting of streptavidin and avidin.

12. The assay of claim 1 wherein the second labeling moiety is selected from the group consisting of a fluorescent moiety, a colorigenic moiety, and a chemiluminescent moiety.

13. The assay of claim 1 wherein the second labeling moiety is acridinium.

14. The assay of claim 13 wherein the detection of the presence of the second labeling moiety is by measuring light emitted from a chemiluminescent reaction utilizing the second labeling moiety.

15. The assay of claim 9 wherein the affinity binding moiety is an IgG2b specific antibody.

* * * * *

SEQUENCE LISTING

```
<160> NUMBER OF SEQ ID NOS: 54

<210> SEQ ID NO 1
<211> LENGTH: 705
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30
```

-continued

```
Gly Thr Ser Asn Lys Leu Thr Gln Leu Gly Thr Phe Glu Asp His Phe
             35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                     85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
             115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445
```

-continued

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Cys Ser His
        675                 680                 685

Leu His Ala Trp Pro Ser Ala Ser Val Ile Ile Thr Ala Ser Ser Cys
    690                 695                 700

His
705

<210> SEQ ID NO 2
<211> LENGTH: 2851
<212> TYPE: DNA
<213> ORGANISM: Homo sapiens

<400> SEQUENCE: 2
cccggcgcag cgcggccgca gcagcctccg ccccccgcac ggtgtgagcg cccgccgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg acccctcggg acggccgggg cagcgctcct ggcgctgctg gtgcgctct      300 gcccggcgag tcgggctctg aggaaaaaga agtttgccca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540

| | |
|---|---|
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga aatcctgcat ggcgccgtgc ggttcagcaa caaccctgcc ctgtgcaatg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctgggtgc aggagaggag aactgccaga aactgaccaa atcatctgt gcccagcagt | 900 |
| gctccgggcg ctgccgtggc aagtccccca gtgactgctg ccacaaccag tgtgctgcag | 960 |
| gctgcacagg cccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgc cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttaggggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgtttgg gacctccggt cagaaaacca aaattataag caacagaggt gaaaacagct | 1740 |
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |
| gcaaccttct ggagggtgag ccaagggagt ttgtggagaa ctctgagtgc atacagtgcc | 1920 |
| acccagagtg cctgcctcag gccatgaaca tcacctgcac aggacgggga ccagacaact | 1980 |
| gtatccagtg tgcccactac attgacggcc cccactgcgt caagacctgc ccggcaggag | 2040 |
| tcatgggaga aaacaacacc ctggtctgga gtacgcaga cgccggccat gtgtgccacc | 2100 |
| tgtgccatcc aaactgcacc tacgggccag gaaatgagag tctcaaagcc atgttattct | 2160 |
| gccttttaa actatcatcc tgtaatcaaa gtaatgatgg cagcgtgtcc caccagagcg | 2220 |
| ggagcccagc tgctcaggag tcatgcttag gatggatccc ttctcttctg ccgtcagagt | 2280 |
| ttcagctggg ttgggtgga tgcagccacc tccatgcctg gccttctgca tctgtgatca | 2340 |
| tcacggcctc ctcctgccac tgagcctcat gccttcacgt gtctgttccc cccgcttttc | 2400 |
| ctttctgcca cccctgcacg tgggccgcca ggttcccaag agtatcctac ccatttcctt | 2460 |
| ccttccactc cctttgccag tgcctctcac cccaactagt agctaaccat cacccccagg | 2520 |
| actgacctct tcctcctcgc tgccagatga ttgttcaaag cacagaattt gtcagaaacc | 2580 |
| tgcagggact ccatgctgcc agccttctcc gtaattagca tggccccagt ccatgcttct | 2640 |
| agccttggtt ccttctgccc ctctgtttga aattctagag ccagctgtgg gacaattatc | 2700 |
| tgtgtcaaaa gccagatgtg aaaacatctc aataacaaac tggctgcttt gttcaatgct | 2760 |
| agaacaacgc ctgtcacaga gtagaaactc aaaaatattt gctgagtgaa tgaacaaatg | 2820 |
| aataaatgca taataaataa ttaaccacca a | 2851 |

```
<210> SEQ ID NO 3
<211> LENGTH: 641
<212> TYPE: PRT
<213> ORGANISM: Homo sapiens

<400> SEQUENCE: 3
```

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

-continued

```
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
        580                 585                 590

Lys Thr Cys Pro Ala Gly Val Met Gly Glu Asn Asn Thr Leu Val Trp
    595                 600                 605

Lys Tyr Ala Asp Ala Gly His Val Cys His Leu Cys His Pro Asn Cys
610                 615                 620

Thr Tyr Gly Pro Gly Asn Glu Ser Leu Lys Ala Met Leu Phe Cys Leu
625                 630                 635                 640

Phe

<210> SEQ ID NO 4
<211> LENGTH: 705
<212> TYPE: PRT
<213> ORGANISM: Homo sapiens

<400> SEQUENCE: 4

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110
```

```
Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525
```

```
Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Arg Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Cys Ser His
        675                 680                 685

Leu His Ala Trp Pro Ser Ala Ser Val Ile Ile Thr Ala Ser Ser Cys
690                 695                 700

His
705

<210> SEQ ID NO 5
<211> LENGTH: 705
<212> TYPE: PRT
<213> ORGANISM: Homo sapiens

<400> SEQUENCE: 5

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190
```

```
Ser Cys Pro Asn Gly Ser Cys Trp Gly Ala Gly Glu Asn Cys Gln
    195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605
```

```
Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Leu Ala Ala Gln Glu Ser Cys Leu Gly Trp Ile Pro
            660                 665                 670

Ser Leu Leu Pro Ser Glu Phe Gln Leu Gly Trp Gly Gly Cys Ser His
        675                 680                 685

Leu His Ala Trp Pro Ser Ala Ser Val Ile Ile Thr Ala Ser Ser Cys
    690                 695                 700

His
705

<210> SEQ ID NO 6
<211> LENGTH: 705
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270
```

-continued

```
Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                    325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                    405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                    485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                    565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
        610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                    645                 650                 655

Gln Ser Gly Ser Pro Ala Ala Gln Glu Ser Cys Leu Gly Trp Ile Pro
                660                 665                 670

Ser Leu Leu Pro Ser Glu Phe Gln Leu Gly Trp Gly Gly Cys Ser His
        675                 680                 685
```

```
Leu His Ala Trp Pro Ser Ala Ser Val Ile Ile Thr Ala Ser Phe Cys
    690             695             700
His
705
```

<210> SEQ ID NO 7
<211> LENGTH: 20
<212> TYPE: DNA
<213> ORGANISM: Homo sapiens

<400> SEQUENCE: 7
tcggggagca gcgatgcgac                                               20

<210> SEQ ID NO 8
<211> LENGTH: 20
<212> TYPE: DNA
<213> ORGANISM: Homo sapiens

<400> SEQUENCE: 8
ccattcgttg gacagccttc                                               20

<210> SEQ ID NO 9
<211> LENGTH: 21
<212> TYPE: DNA
<213> ORGANISM: Homo sapiens

<400> SEQUENCE: 9
gtcatgggag aaaacaacac c                                             21

<210> SEQ ID NO 10
<211> LENGTH: 20
<212> TYPE: DNA
<213> ORGANISM: Homo sapiens

<400> SEQUENCE: 10
agtaatgatg gcagcgtgtc                                               20

<210> SEQ ID NO 11
<211> LENGTH: 20
<212> TYPE: DNA
<213> ORGANISM: Homo sapiens

<400> SEQUENCE: 11
tcgctgccag atgattgttc                                               20

<210> SEQ ID NO 12
<211> LENGTH: 20
<212> TYPE: DNA
<213> ORGANISM: Homo sapiens

<400> SEQUENCE: 12
cgctctggtg ggacacgctg                                               20

<210> SEQ ID NO 13
<211> LENGTH: 20
<212> TYPE: DNA
<213> ORGANISM: Homo sapiens

<400> SEQUENCE: 13
gaaggaacca aggctagaag                                               20

```
<210> SEQ ID NO 14
<211> LENGTH: 17
<212> TYPE: PRT
<213> ORGANISM: Homo sapiens

<400> SEQUENCE: 14

Leu Glu Asn Leu Gln Ile Ile Arg Gly Asn Met Tyr Tyr Glu Asn Ser
1               5                   10                  15
Tyr

<210> SEQ ID NO 15
<211> LENGTH: 23
<212> TYPE: PRT
<213> ORGANISM: Homo sapiens

<400> SEQUENCE: 15

Asp Ser Tyr Glu Asn Ile Glu Glu Asp Gly Val Arg Lys Cys Lys Lys
1               5                   10                  15
Cys Glu Gly Pro Cys Arg Lys
            20

<210> SEQ ID NO 16
<211> LENGTH: 18
<212> TYPE: PRT
<213> ORGANISM: Homo sapiens

<400> SEQUENCE: 16

Phe Arg Gly Asp Ser Phe Thr His Thr Pro Pro Leu Asp Pro Gln Glu
1               5                   10                  15
Leu Asp

<210> SEQ ID NO 17
<211> LENGTH: 12
<212> TYPE: PRT
<213> ORGANISM: Homo sapiens

<400> SEQUENCE: 17

Ile Gln Cys Ala His Tyr Ile Asp Gly Pro His Cys
1               5                   10

<210> SEQ ID NO 18
<211> LENGTH: 31
<212> TYPE: PRT
<213> ORGANISM: Homo sapiens

<400> SEQUENCE: 18

Ser Val Ser His Gln Ser Gly Ser Pro Ala Ala Gln Glu Ser Cys Leu
1               5                   10                  15
Gly Trp Ile Pro Ser Leu Leu Pro Ser Glu Phe Gln Leu Gly Trp
            20                  25                  30

<210> SEQ ID NO 19
<211> LENGTH: 24
<212> TYPE: PRT
<213> ORGANISM: Homo sapiens

<400> SEQUENCE: 19

Gly Gly Cys Ser His Leu His Leu His Ala Trp Pro Ser Ala Ser Val
1               5                   10                  15
Ile Ile Thr Ala Ser Ser Cys His
            20
```

```
<210> SEQ ID NO 20
<211> LENGTH: 34
<212> TYPE: PRT
<213> ORGANISM: Homo sapiens

<400> SEQUENCE: 20

Ala Asn Cys Thr Tyr Gly Cys Ala Gly Pro Gly Leu Gln Gly Cys Glu
1               5                   10                  15

Val Trp Pro Ser Gly Tyr Val Glu Trp Gln Trp Ile Leu Lys Thr Phe
            20                  25                  30

Trp Ile

<210> SEQ ID NO 21
<211> LENGTH: 53
<212> TYPE: PRT
<213> ORGANISM: Homo sapiens

<400> SEQUENCE: 21

Gly Pro Asp Asn Cys Ile Gln Cys Ala His Tyr Ile Asp Gly Pro His
1               5                   10                  15

Cys Val Lys Thr Cys Pro Ala Gly Val Met Gly Glu Asn Asn Thr Leu
            20                  25                  30

Val Trp Lys Tyr Ala Asp Ala Gly His Val Cys His Leu Cys His Pro
        35                  40                  45

Asn Cys Thr Tyr Gly
    50

<210> SEQ ID NO 22
<211> LENGTH: 74
<212> TYPE: PRT
<213> ORGANISM: Homo sapiens

<400> SEQUENCE: 22

His Ala Ser Ser Asn Leu Leu Val Ser Arg Pro Gln Cys Ser Gly Asn
1               5                   10                  15

Asp Ser Ala Met His Arg Val Pro Gly Arg Ala Cys Val Val Gln Cys
            20                  25                  30

Cys Thr Ser Gln Gln Glu Gly Arg Gly Thr Lys Glu His Arg Ser Trp
        35                  40                  45

Gln Leu Pro Gln Ser Pro Gly Ala Phe Ala Phe Leu Ser Arg Phe Leu
    50                  55                  60

Arg Leu Thr Trp Gly Leu Ala Val Leu Gln
65                  70

<210> SEQ ID NO 23
<211> LENGTH: 12
<212> TYPE: PRT
<213> ORGANISM: Homo sapiens

<400> SEQUENCE: 23

Phe Leu Arg Leu Thr Trp Gly Leu Ala Val Leu Gln
1               5                   10

<210> SEQ ID NO 24
<211> LENGTH: 4
<212> TYPE: PRT
<213> ORGANISM: Homo sapiens

<400> SEQUENCE: 24

Lys Thr Ile Ile
1
```

```
<210> SEQ ID NO 25
<211> LENGTH: 24
<212> TYPE: PRT
<213> ORGANISM: Homo sapiens

<400> SEQUENCE: 25

Cys Ala Ser Val Ser Leu His Gln Tyr Leu Tyr Ile Ser Ile Ser Val
1               5                   10                  15

Ser Val Ser Ile Cys Cys Trp Ala
            20

<210> SEQ ID NO 26
<211> LENGTH: 11
<212> TYPE: PRT
<213> ORGANISM: Homo sapiens

<400> SEQUENCE: 26

Met Cys Asp Tyr Ile Pro Asp Ser Glu Pro Phe
1               5                   10

<210> SEQ ID NO 27
<211> LENGTH: 54
<212> TYPE: PRT
<213> ORGANISM: Homo sapiens

<400> SEQUENCE: 27

Ile Tyr Asp Val His Asn Ile Pro Glu Tyr Ile Val Ser Leu Ile Ser
1               5                   10                  15

Gln Met Gly Cys Ile Ala Phe Ser Ile Ser Ile Val Lys Glu Thr Leu
            20                  25                  30

Thr Gly Val Ser Leu Thr Thr Cys Glu Gln Gln His Gln Ser Pro Asp
        35                  40                  45

Tyr Ser Ile Ser Ser Cys
    50

<210> SEQ ID NO 28
<211> LENGTH: 19
<212> TYPE: PRT
<213> ORGANISM: Homo sapiens

<400> SEQUENCE: 28

Trp Asp Val Leu Pro Ser Pro Phe Leu Leu Leu Lys Lys His Leu Gln
1               5                   10                  15

Gly Phe Leu

<210> SEQ ID NO 29
<211> LENGTH: 67
<212> TYPE: PRT
<213> ORGANISM: Homo sapiens

<400> SEQUENCE: 29

Val Thr Glu Gly Leu Ile Ser Val Ser Arg Ser Pro Ser Pro Ser Asp
1               5                   10                  15

Ala Leu Thr Ser Phe Ser Pro Ala Pro Ser Cys His Cys Pro Cys
            20                  25                  30

Pro Ala Ser Leu Gln Gly Ser Thr Gly Leu Pro Phe Pro Thr Ser Leu
        35                  40                  45

Ser Gln Leu Leu Val Ser Asn Pro Tyr Gly Cys Pro Lys Ala Phe Ser
    50                  55                  60

Glu Pro Ala
65
```

```
<210> SEQ ID NO 30
<211> LENGTH: 28
<212> TYPE: PRT
<213> ORGANISM: Homo sapiens

<400> SEQUENCE: 30

Pro Val Leu Pro Leu Ser Leu Ser Ser Phe Ser Ser Arg Val Asn Trp
1               5                   10                  15

Ser Thr Phe Pro Tyr Lys Ser Val Thr Ala Ser Cys
            20                  25

<210> SEQ ID NO 31
<211> LENGTH: 78
<212> TYPE: PRT
<213> ORGANISM: Homo sapiens

<400> SEQUENCE: 31

Pro Gly Asn Glu Ser Leu Lys Ala Met Leu Phe Cys Leu Phe Lys Leu
1               5                   10                  15

Ser Ser Cys Asn Gln Ser Asn Asp Gly Ser Val Ser His Gln Ser Gly
            20                  25                  30

Ser Pro Ala Ala Gln Glu Ser Cys Leu Gly Trp Ile Pro Ser Leu Leu
        35                  40                  45

Pro Ser Glu Phe Gln Leu Gly Trp Gly Cys Ser His Leu His Ala
    50                  55                  60

Trp Pro Ser Ala Ser Val Ile Ile Thr Ala Ser Ser Cys His
65                  70                  75

<210> SEQ ID NO 32
<211> LENGTH: 75
<212> TYPE: PRT
<213> ORGANISM: Homo sapiens

<400> SEQUENCE: 32

Val Ser Ala Gly Leu Gly Trp Met Gln Pro Pro Cys Leu Ala Phe
1               5                   10                  15

Cys Ile Cys Asp His His Gly Leu Leu Leu Pro Leu Ser Leu Met Pro
            20                  25                  30

Ser Arg Val Cys Ser Pro Arg Phe Ser Phe Leu Pro Pro Leu His Val
        35                  40                  45

Gly Arg Gln Val Pro Lys Ser Ile Leu Pro Ile Ser Phe Leu Pro Leu
    50                  55                  60

Pro Leu Pro Val Pro Leu Thr Pro Thr Ser Ser
65                  70                  75

<210> SEQ ID NO 33
<211> LENGTH: 13
<212> TYPE: PRT
<213> ORGANISM: Homo sapiens

<400> SEQUENCE: 33

Cys Thr Gly Pro Gly Leu Glu Gly Cys Pro Thr Asn Gly
1               5                   10

<210> SEQ ID NO 34
<211> LENGTH: 79
<212> TYPE: PRT
<213> ORGANISM: Homo sapiens
```

<400> SEQUENCE: 34

His Thr Ala Gln Gln Arg Gln Lys Gly Phe Leu Gln His Gln Leu Trp
1               5                   10                  15

Pro Val Cys Gln Ser Lys Ala Leu Arg Lys Ala Arg Leu Lys Ser Leu
                20                  25                  30

Ile Gln Thr His Gln Glu Arg Val Val Leu Ser Met Ala Ser Ser
            35                  40                  45

Gln Glu Ser Trp Asn Thr Tyr Pro Ser Thr Cys Leu Pro Phe Trp Met
    50                  55                  60

Phe Pro Asn Met Asn Gln Thr Ser Arg Pro Leu Cys His Leu Trp
65                  70                  75

<210> SEQ ID NO 35
<211> LENGTH: 19
<212> TYPE: PRT
<213> ORGANISM: Homo sapiens

<400> SEQUENCE: 35

Glu Leu Leu Gly His Pro Ala Glu Leu Pro His Ser Thr Leu Gln Ser
1               5                   10                  15

Gln Gly Ser

<210> SEQ ID NO 36
<211> LENGTH: 17
<212> TYPE: PRT
<213> ORGANISM: Homo sapiens

<400> SEQUENCE: 36

Ser Tyr Ile Val Ser His Phe Pro Arg Ser Phe Tyr Lys Met Ser Val
1               5                   10                  15

His

<210> SEQ ID NO 37
<211> LENGTH: 47
<212> TYPE: PRT
<213> ORGANISM: Homo sapiens

<400> SEQUENCE: 37

Pro Lys Ile Pro Ser Ile Ala Thr Gly Met Val Gly Ala Leu Leu Leu
1               5                   10                  15

Leu Leu Val Val Ala Leu Gly Ile Gly Leu Phe Met Arg Arg Arg His
                20                  25                  30

Ile Val Arg Lys Arg Thr Leu Arg Arg Leu Leu Gln Glu Arg Glu
            35                  40                  45

<210> SEQ ID NO 38
<211> LENGTH: 161
<212> TYPE: DNA
<213> ORGANISM: Homo sapiens

<400> SEQUENCE: 38
cagggaccag acaactgtat ccagtgtgcc cactacattg acggcccca ctgcgtcaag      60 acctgcccgg caggagtcat gggagaaaac aacaccctgg tctggaagta cgcagacgcc    120
ggccatgtgt gccacctgtg ccatccaaac tgcacctacg g                        161

<210> SEQ ID NO 39
<211> LENGTH: 230
<212> TYPE: DNA
<213> ORGANISM: Homo sapiens

<400> SEQUENCE: 39

```
cagccatgcc agtagcaact tgcttgtgag caggcctcag tgcagtggga atgactctgc      60
catgcaccgt gtccccggcc gggccgtgtg ttgtgcaatg ctgcacatca caacaggagg     120 gtaggggac aaaagagcac aggtcctggc agctgccaca gtctccaggg gcttttgcgt     180
ttctctccag atttctaagg ttaacatggg gattagctgt tttgcaatga                 230
```

<210> SEQ ID NO 40
<211> LENGTH: 43
<212> TYPE: DNA
<213> ORGANISM: Homo sapiens

<400> SEQUENCE: 40

```
cagatttcta aggttaacat ggggattagc tgttttgcaa tga                        43
```

<210> SEQ ID NO 41
<211> LENGTH: 19
<212> TYPE: DNA
<213> ORGANISM: Homo sapiens

<400> SEQUENCE: 41

```
taggaaaaca atcatataa                                                   19
```

<210> SEQ ID NO 42
<211> LENGTH: 79
<212> TYPE: DNA
<213> ORGANISM: Homo sapiens

<400> SEQUENCE: 42

```
tagatgtgca tcagtatctc tgcatcaata tctctatatc agtatctctg tgtcagtgag      60
catatgttgc tgggcttag                                                   79
```

<210> SEQ ID NO 43
<211> LENGTH: 40
<212> TYPE: DNA
<213> ORGANISM: Homo sapiens

<400> SEQUENCE: 43

```
tagtatgtgt gattacattc ctgattctga gccttttag                             40
```

<210> SEQ ID NO 44
<211> LENGTH: 169
<212> TYPE: DNA
<213> ORGANISM: Homo sapiens

<400> SEQUENCE: 44

```
gagtatttat gacgtgcaca acattcctga atatattctc tctctcattt ctcagatggg      60
atgtattgcc ttctccattt ctattgttaa agaaacactt acagggtttt ctttaacaac     120
ttgtgaacag cagcatcaga gcccagacta cagcataagc agctgctga                 169
```

<210> SEQ ID NO 45
<211> LENGTH: 64
<212> TYPE: DNA
<213> ORGANISM: Homo sapiens

<400> SEQUENCE: 45

```
cagatgggat gtattgcctt ctccatttct attgttaaag aaacacttac aggggtttct      60
ttaa                                                                   64
```

<210> SEQ ID NO 46
<211> LENGTH: 208
<212> TYPE: DNA
<213> ORGANISM: Homo sapiens

<400> SEQUENCE: 46

```
cagagttacc gagggcctca tcagcgtcag caggagcccc tcgccttctg acgctctcac      60
atccttctct cctgcagccc cgtcctgcca ctgtccttgt ccagcttctc ttcaagggtc     120
aactggtcta cctttcccta caagtctgtc acagcttctt gttagcaatc cctatggttg     180
cccaaaagca ttttcagagc ctgcataa                                        208
```

<210> SEQ ID NO 47
<211> LENGTH: 91
<212> TYPE: DNA
<213> ORGANISM: Homo sapiens

<400> SEQUENCE: 47

```
cagccccgtc ctgccactgt ccttgtccag cttctcttca agggtcaact ggtctacctt      60
tccctacaag tctgtcacag cttcttgtta g                                     91
```

<210> SEQ ID NO 48
<211> LENGTH: 240
<212> TYPE: DNA
<213> ORGANISM: Homo sapiens

<400> SEQUENCE: 48

```
caggccagga aatgagagtc tcaaagccat gttattctgc cttttaaac tatcatcctg       60
taatcaaatg aatgatggca gcgtgtccca ccagagcggg agcccagcgc gcaggagtca     120
tgcttaggat ggatcccttc tcttctgccg tcagagtttc agctgggttg gggtggatgc     180
agccacctcc atgcctggcc ttctgcatct gtgatcatca cggcctcctc ctgccactga     240
```

<210> SEQ ID NO 49
<211> LENGTH: 232
<212> TYPE: DNA
<213> ORGANISM: Homo sapiens

<400> SEQUENCE: 49

```
cagagtttca gctgggttgg ggtggatgca gccacctcca tgcctggcct tctgcatctg      60
tgatcatcac ggcctcctcc tgccactgag cctcatgcct tcacgtgtct gttccccccg     120
cttttccttt ctgccacccc tgcacgtggg ccgccaggtt cccaagagta tcctacccat     180
ttccttcctt ccactccctt tgccagtgcc tctcacccca actagtagct aa              232
```

<210> SEQ ID NO 50
<211> LENGTH: 42
<212> TYPE: DNA
<213> ORGANISM: Homo sapiens

<400> SEQUENCE: 50

```
cagatgcact gggccaggtc ttgaaggctg tccaacgaat gg                          42
```

<210> SEQ ID NO 51
<211> LENGTH: 244
<212> TYPE: DNA
<213> ORGANISM: Homo sapiens -continued

```
<400> SEQUENCE: 51
cagacacact gcccagcaaa ggcaaaaggg cttccttcaa catcagctct ggccagtttg      60
ccagagcaaa gccctgagaa aagcaaggtt gaaaagtctt attcaaactc accaggaaag     120
agtggtgtta ctctcgatgg cgtctagcca ggaatcatgg aattatacac cgagcacctg    180
tttgccattt tggatgtttc caaacatgaa ccaaacttcc aggcccctct gccatctctg    240
gtaa                                                                  244

<210> SEQ ID NO 52
<211> LENGTH: 64
<212> TYPE: DNA
<213> ORGANISM: Homo sapiens

<400> SEQUENCE: 52
cagtgagctg ctaggacacc cagcagaact tccccactcc acactgcaat ctcagggatc     60
ttag                                                                  64

<210> SEQ ID NO 53
<211> LENGTH: 58
<212> TYPE: DNA
<213> ORGANISM: Homo sapiens

<400> SEQUENCE: 53
tagaagctac atagtgtctc actttccaag atcattctac aagatgtcag tgcactga       58

<210> SEQ ID NO 54
<211> LENGTH: 145
<212> TYPE: DNA
<213> ORGANISM: Homo sapiens

<400> SEQUENCE: 54
caggcctaag atcccgtcca tcgccactgg gatggtgggg gccctcctct tgctgctggt     60
ggtggccctg gggatcggcc tcttcatgcg aaggcgccac atcgttcgga agcgcacgct    120
gcggaggctg ctgcaggaga gggag                                          145
```